United States Patent
Lu et al.

(10) Patent No.: US 7,869,664 B2
(45) Date of Patent: Jan. 11, 2011

(54) SYSTEMS AND METHODS FOR ALIGNMENT OF OBJECTS IN IMAGES

(75) Inventors: Peng Lu, Mountain View, CA (US); Ming Zheng, Mountain View, CA (US); Guochun Liao, Belmont, CA (US)

(73) Assignee: F. Hoffmann-La Roche AG, Basel (CH)

( * ) Notice: Subject to any disclaimer, the term of this patent is extended or adjusted under 35 U.S.C. 154(b) by 873 days.

(21) Appl. No.: 11/820,939

(22) Filed: Jun. 21, 2007

(65) Prior Publication Data

US 2008/0317307 A1    Dec. 25, 2008

(51) Int. Cl.
*G06K 9/32* (2006.01)
*G06K 9/00* (2006.01)

(52) U.S. Cl. ....................... 382/294; 382/128
(58) Field of Classification Search ......... 382/128–134, 382/173, 165, 286–187, 289, 294, 296, 305, 382/312; 702/20; 345/651, 662, 677; 436/518
See application file for complete search history.

(56) References Cited

U.S. PATENT DOCUMENTS 5,873,052 A * 2/1999 Sharaf ........................ 702/20
7,263,220 B2 * 8/2007 Crandall et al. ............. 382/165

2004/0142496 A1    7/2004 Nicholson et al.

FOREIGN PATENT DOCUMENTS

WO    WO 02/057958 A1    7/2002

OTHER PUBLICATIONS

Ewens et al., 2006, "Doxorubicin plus Interleukin-2 Chemoimmunotherapy against Breast Cancer in Mice," Cancer Res 66: 5419-5426.
Sim et al., 2001, "Two-Dimensional Object Alignment Based on the Robust Oriented Hausdorff Similarity Measure," IEEE Transactions on Image Processing 10: 475-483.
Lu et al., 2007, "Global metabolic changes following loss of a feedback loop reveal dynamic steady states of the yeast metabolome," ScienceDirect Metabolic Engineering 9: 8-20.
Danish Patent and Trademark Office, Singapore Examination Report dated Mar. 30, 2010 for application No. SG 200804737-5.
Danish Patent and Trademark Office, Singapore Written Opinion dated Jun. 25, 2009 for Singapore patent application No. 200804737-5.

* cited by examiner

*Primary Examiner*—Kanji Patel
(74) *Attorney, Agent, or Firm*—Jones Day; Brett Lovejoy

(57) ABSTRACT

Systems and methods for aligning objects in object sets are provided. An object set has objects that are in a corresponding image in a plurality of images. For each respective object in a first object set, a corresponding object group is constructed that contains the respective object, thereby constructing a plurality of object groups. Similarity metrics are computed between object groups and objects in objects sets in order to assign the objects to object groups. The object groups are then refined in order to align objects in the object sets.

55 Claims, 7 Drawing Sheets

Initial alignment proposal

|  | Image 1 | Image 2 |  |
|---|---|---|---|
| Object Group A | Object X | Object H | $F$ (alignment proposal) of current alignment proposal |
| Object Group B | Object Y | Object J |  |
| Object Group C | Object Z | Object K |  |

Alternate alignment proposal 1

|  | Image 1 | Image 2 |  |
|---|---|---|---|
| Object Group A | Object X | Object H | $F$ (alignment proposal) of alternate alignment proposal 1 |
| Object Group B | Object Z | Object J |  |
| Object Group C | Object Y | Object K |  |

Alternate alignment proposal 2

|  | Image 1 | Image 2 |  |
|---|---|---|---|
| Object Group A | Object Y | Object H | $F$ (alignment proposal) of alternate alignment proposal 2 |
| Object Group B | Object X | Object J |  |
| Object Group C | Object Z | Object K |  |

Alternate alignment proposal 3

|  | Image 1 | Image 2 |  |
|---|---|---|---|
| Object Group A | Object Y | Object H | $F$ (alignment proposal) of alternate alignment proposal 3 |
| Object Group B | Object Z | Object J |  |
| Object Group C | Object X | Object K |  |

Alternate alignment proposal 4

|  | Image 1 | Image 2 |  |
|---|---|---|---|
| Object Group A | Object Z | Object H | $F$ (alignment proposal) of alternate alignment proposal 4 |
| Object Group B | Object Y | Object J |  |
| Object Group C | Object X | Object K |  |

Alternate alignment proposal 5

|  | Image 1 | Image 2 |  |
|---|---|---|---|
| Object Group A | Object Z | Object H | $F$ (alignment proposal) of alternate alignment proposal 5 |
| Object Group B | Object X | Object J |  |
| Object Group C | Object Y | Object K |  |

Figure 5

SYSTEMS AND METHODS FOR ALIGNMENT OF OBJECTS IN IMAGES

BACKGROUND OF THE INVENTION

1. Field of Invention

This invention relates to processes, apparatus, media and signals for automatically aligning objects in images, such as peaks in two-dimensional nuclear magnetic resonance spectra.

2. Description of Related Art

Object matching in images, also known as image alignment, has been an important topic in computer vision, object recognition, and image analysis. The performance of the matching method depends on the properties of the features and the matching measure used. One application where object matching in images can be performed is in the analysis of nuclear magnetic resonance (NMR) spectra and the alignment of equivalent peaks in such spectra to each other.

An NMR spectrum typically comprises a one-dimensional or multi-dimensional image that consists of objects that represent molecular features of a sample. Examples of molecular features of a sample include, but are not limited to, the presence of specific metabolites or other molecules within the sample. The use of NMR spectroscopy (NMR) for analyzing complex biological samples and comparing them to each other has a long history in medical applications. For example, comparative metabolic profiling of the endogenous metabolites produced by an individual (metabonomics) using NMR has been utilized in the early prediction of response to doxorubicin and interleukin-2 treatment. See, Ewens et al., 2006, Cancer Res. 66, 5419. Many metabonomics studies using NMR are based on one dimensional $^1$H NMR, which has less sample acquisition time and is easy to analyze. However, the high spectral congestion of 1H NMR spectra from complex biological samples limits the number of metabolites that can be uniquely identified and quantified.

Recently, two-dimensional $^1$H—$^{13}$C NMR was used for analyzing global metabolic changes in the yeast metabolome. See, Peng, 2007, Metabolic Engineering 9, 8-20. Because almost all endogenous metabolites contain carbon, the second $^{13}$C NMR dimension provides a greatly extended spectral range (~200 parts per million) and enables separation and accurate identification of many metabolites that congest into a single object along the $^1$H NMR dimension. However, comparing NMR metabolic profiles requires aligning NMR objects (peaks) representing the same metabolites across multiple spectra. The nature of $^1$H—$^{13}$C NMR poses a couple of challenges. First, the position of an object representing the same metabolite across samples or replicates is not fixed in the two-dimensional $^1$H—$^{13}$C NMR spectra. There is always slight position shifting observed because the experimental condition cannot be one hundred percent identical when each spectrum is measured: a slight difference in experimental conditions, such as pH, will cause an object to shift. Even for replicates from the same sample, such a shift is inevitable. Second, these shifts are not systematic. The direction and extent of the shift for each object is not consistent throughout a spectrum. The objects can shift towards different directions with different extent in the different areas of a spectrum. Furthermore, not all metabolites are present in all samples, so the capability to align an insignificant signal but not its neighboring significant signal to objects representing the same metabolite is desirable.

Thus, for the foregoing reasons, comparison of multidimensional NMR metabolic profiles presents a classic problem: the alignment of objects in images. In NMR, the objects are peaks that appear in the NMR spectra. Many images, such as NMR metabolic profiles, exhibit characteristics that can be exploited in order to align objects in the images. For example, although the object shifting of the NMR spectrum is globally inconsistent, the objects within a small region of the same spectrum display similar shifting patterns, in which such objects shift towards similar directions with similar extent. As a result, the local patterns across different spectra are usually matched. Conventional processes for aligning objects in images do not satisfactorily exploit these patterns of matched local shift. Accordingly, what are needed in the art are improved processes, apparatus, media and signals for aligning objects in a plurality images that take advantage of patterns of matched local shift.

SUMMARY OF THE INVENTION

Provided are improved processes, apparatus, media and signals for aligning objects in a plurality of images. The improved processes, apparatus, media and signals for aligning objects in a plurality of images can be used for general point alignment problems in N-dimensional images such as two-dimensional NMR spectra. Advantageously, the improved processes, apparatus, media and signals for aligning objects in a plurality of images take advantage of patterns of matched local shift.

One embodiment provides a method for aligning objects, such as peaks, in a plurality of object sets. Each such object set comprises the objects found in a corresponding image (e.g., NMR spectrum) in a plurality of images. For example, the plurality of images can be a plurality of two-dimensional NMR spectra, where each respective spectrum has a corresponding object set that contains all the peaks in the respective spectrum (or a selected subset of the peaks in the spectrum). The method comprises constructing, for each respective object in a first object set in the plurality of object sets, a corresponding object group that contains the respective object in the first object set, thereby constructing a plurality of object groups. Thus, at this initial stage, the plurality of object groups comprises one object group for each unique object in a particular (first) object set. In other words, since each object set corresponds to an image, at this initial stage, the plurality of object groups comprise one object group for each unique object in a particular image (the image that corresponds to the first object set). Next, for each respective object in an object set in the plurality of object sets, a plurality of similarity metrics are computed. Each such similarity metric is between (i) the respective object and (ii) objects in an object group in the plurality of object groups. The purpose of such a computation is to determine which object group to place the respective object. The respective object is added to a first object group in the plurality of object groups when two conditions are satisfied. First, the similarity metric between the respective object and objects in the first object group must be better than the similarity metric between the respective object and objects in any other object group in the plurality of object groups. Second, coordinate differences between the respective object and objects in the first object group must be below threshold values. Otherwise, if these conditions do not hold true, a new object group is created and the respective object group is added to the newly created object group. The process of assigning objects to object groups is repeated for each remaining object set in the plurality of object sets. In this manner, objects that are in the same object group are deemed to correspond to each other. In this way, objects in the plurality of object sets are aligned.

A first object in a first object set is aligned to a second object in a second object set when the first object and the second object represent the same observable in the two object sets. For example, if the first object represents the presence or the abundance of a particular metabolite, than the second object also represents the presence or the abundance of the particular metabolite when the first and second object are aligned (correlated). Of course, the first object may represent the presence or the abundance of the particular metabolite in a different biological sample than the second object and still be aligned to the second object. Thus, the alignment or identification of correspondence between objects in the present invention is an assignment operation. For a plurality of object sets, each containing a plurality of objects, the systems and methods of the present invention determine which objects in the plurality of objects are equivalent (represent the same observable). The process of addressing this question for as many of the objects in the object sets as possible is an alignment process. When this alignment process is complete, certain objects in the objects sets are deemed to be aligned (correlated) to each other.

In some embodiments, each object in an object group or object set is characterized by a first dimension value X and a second dimension value Y. In some embodiments, the first dimension value X corresponds to the nuclear magnetic resonance of carbon ($^{13}C$) atoms, and the second dimension value Y corresponds to the nuclear magnetic resonance of hydrogen ($^1H$) atoms, and the coordinate differences between the respective object and an object in the first object group is below threshold values when $|C^2 - C^1| < B_C$, and $|H^2 - H^1| < B_H$ where
 $C^2$ is the first dimension indicator for the respective object;
 $C^1$ is the first dimension indicator for the object in the first object group;
 $H^2$ is the second dimension indicator for the respective object;
 $H^1$ is the second dimension indicator for the object in the first object group;
 $B_C$ is the first dimension threshold limit; and
 $B_H$ is the second dimension threshold limit.

In some embodiments, each image in the plurality of images is a two-dimensional image. In some embodiments, each image in the plurality of images is an N-dimensional image, where N is equal to 1 or greater. In some embodiments, a coordinate difference between the respective object and an object in the first object group is below threshold values when $|C_1^2 - C_1^1| < B_1$, $|C_2^2 - C_2^1| < B_2$

...

$|C_N^2 - C_N^1| < B_N$ where
 $C_i^2$ is the $i^{th}$ dimension indicator for the respective object;
 $C_i^1$ is the $i^{th}$ dimension indicator for the object in the first object group; and
 $B_i$ is the $i^{th}$ dimension threshold limit.

In some embodiments, each image in the plurality of images is a two-dimensional image. In some embodiments, an image in the plurality of images is a two-dimensional $^1H$—$^{13}C$ nuclear magnetic resonance spectrum and the objects in the image are peaks in the two-dimensional $^1H$—$^{13}C$ nuclear magnetic resonance spectrum. In some embodiments, an image in the plurality of images is a two-dimensional nuclear magnetic resonance (NMR) spectrum, a three-dimensional NMR spectrum, or a four-dimensional NMR spectrum and the objects in the image are peaks in the NMR spectrum. In some embodiments, an image in the plurality of images is a two-dimensional heteronuclear or homonuclear magnetic resonance spectrum and objects in the image are peaks in the two-dimensional heteronuclear or homonuclear magnetic resonance spectrum. In some embodiments, an object set in the plurality of object sets comprises 50 objects, 200 objects, 1000 objects, or 10000 objects.

In some embodiments, the plurality of images comprise $^1H$—$^{13}C$ nuclear magnetic resonance spectra, and a similarity metric is computed between a respective object and an object in an object group in the plurality of object groups according to the formula:

$$\text{sim}(\vec{p}_i, \vec{p}_j) = -\{\text{dist}(\vec{p}_i, \vec{p}_j)\}^2 = -\{(C_i - C_j)^2 + \lambda(H_i - H_j)^2\}$$

where
 $\text{sim}(\vec{p}_i, \vec{p}_j)$ is the similarity metric between the respective object $\vec{p}_i$ and an object $\vec{p}_j$ in the object group;
 $C_i$ is the coordinate of $\vec{p}_i$ in the $^{13}C$ dimension;
 $C_j$ is the coordinate of $\vec{p}_j$ in the $^{13}C$ dimension;
 $H_i$ is the coordinate of $\vec{p}_i$ in the $^1H$ dimension;
 $H_j$ is the coordinate of $\vec{p}_j$ in the $^1H$ dimension; and
 $\lambda$ is a normalizing constant.

In some embodiments, the similarity metric between the respective object and objects in the first object group is better than the similarity metric between the respective object and objects of any other object group in the plurality of object groups when the similarity metric between the respective object and objects in the first object group is greater than the similarity metric between the respective object and the objects in any other object group in the plurality of object groups.

In some embodiments, the method further comprises optimizing the assignment of objects in the plurality of object groups. For example, one optimization approach comprises (i) selecting a subcombination of object groups in the plurality of object groups, (ii) selecting the subcombination of objects from an object set in the plurality of objects sets that are assigned to the subcombination of object groups, (iii) computing a similarity score for each possible object—object group combination of the selected subcombination of objects and the selected subcombination of object groups, and (iv) reassigning the selected subcombintation of objects in the object set to object groups in the selected subcombination of object groups based upon the object—object group combination that achieved the best similarity score in step (iii). In some embodiments, steps (ii), (iii) and (iv) are repeated for each object set in the plurality of object sets. In some embodiments, steps (i), (ii), (iii), and (iv) are repeated for a different subcombination of object groups in the plurality of object groups. In some embodiments, steps (ii), (iii), and (iv) are repeated for each object set in the plurality of object sets with the given different subcombination of object groups in the plurality of object groups.

In some embodiments, steps (i), (ii), (iii), and (iv) are repeated several times, and each repetition of steps (i), (ii), (iii), and (iv) is for a different subcombination of object groups in the plurality of object groups.

In some embodiments, the optimization method further comprises (v) repeating steps (ii), (iii) and (iv) for each object set in the plurality of object sets, and (vi) determining whether a value for an objective function has improved relative to a value for the objective function before step (v). If the objective function has improved, steps (i), (ii), (iii), and (iv) are repeated for a different subcombination of object groups in the plurality of object groups. If the objective function has not improved, the optimization is terminated. In some embodiments, the objective function, optionally denoted F (alignment proposal), is:

$$F(\text{alignment proposal}) = \sum_{k=1,\, \text{all object groups in the plurality of objects groups}} f(\text{object group}_k)$$

where $$f(\text{object group}_k) = \sum_{\text{all pairs } \langle i,j \rangle \text{ in object group } k} \text{sim}(\vec{p}_i, \vec{p}_j)$$

In some embodiments, the plurality of images comprises a $^1\text{H}-^{13}\text{C}$ nuclear magnetic resonance spectrum and $$\text{sim}(\vec{p}_i, \vec{p}_j) = -\{\text{dist}(\vec{p}_i, \vec{p}_j)\}^2 = -\{(C_i - C_j)^2 + \lambda(H_i - H_j)^2\},$$
where $C_i$ is the coordinate of object $\vec{p}_i$ in object group k in the $^{13}$C dimension;

$C_j$ is the coordinate of object $\vec{p}_j$ in object group k in the $^{13}$C dimension;

$H_i$ is the coordinate of object $\vec{p}_i$ in object group k in the $^1$H dimension;

$H_j$ is the coordinate of object $\vec{p}_j$ in object group k in the $^1$H dimension; and $\lambda$ is a normalizing constant.

In some embodiments, the plurality of images comprises a two-dimensional spectrum and $$\text{sim}(\vec{p}_i, \vec{p}_j) = -\{\text{dist}(\vec{p}_i, \vec{p}_j)\}^2 = -\{(X_i - X_j)^2 + \lambda(Y_i - Y_j)^2\},$$
where $X_i$ is the coordinate of object $\vec{p}_i$ in object group k in the X dimension;

$X_j$ is the coordinate of object $\vec{p}_j$ in object group k in the X dimension;

$Y_i$ is the coordinate of object $\vec{p}_i$ in object group k in the Y dimension;

$Y_j$ is the coordinate of object $\vec{p}_j$ in object group k in the Y dimension; and $\lambda$ is a normalizing constant.

In some embodiments, the plurality of images comprises a two-dimensional spectrum and $$\text{sim}(\vec{p}_i, \vec{p}_j) = \begin{cases} -\infty, & \text{if } |X_i - X_j| \text{ or } |Y_i - Y_j| \text{ is larger than an upper bound, and} \\ -\{\text{dist}(\vec{p}_i, \vec{p}_j)\}^2, & \text{otherwise,} \end{cases}$$

where $-\{\text{dist}(\vec{p}_i, \vec{p}_j)\}^2 = -\{(X_i - X_j)^2 + \lambda(Y_i - Y_j)^2\};$ $X_i$ is the coordinate of object $\vec{p}_i$ in object group k in the X dimension;

$X_j$ is the coordinate of object $\vec{p}_j$ in object group k in the X dimension;

$Y_i$ is the coordinate of object $\vec{p}_i$ in object group k in the Y dimension;

$Y_j$ is the coordinate of object $\vec{p}_j$ in object group k in the Y dimension; and $\lambda$ is a normalizing constant.

In some embodiments, the plurality of images comprises a two-dimensional spectrum and $$\text{sim}(\vec{p}_i, \vec{p}_j) = \begin{cases} -\infty, & \text{if } |X_i - Y_j| \text{ or } |X_i - Y_j| \text{ is larger than an upper bound, and} \\ -\{\text{dist}(\vec{p}_i, \vec{p}_j)\}^2 + \gamma \cdot \text{correlation}_{ij} - \eta \cdot (I_i - I_j)^2, & \text{otherwise,} \end{cases}$$

where $-\{\text{dist}(\vec{p}_i, \vec{p}_j)\}^2 = -\{(X_i - X_j)^2 + \lambda(Y_i - Y_j)^2\};$ $X_i$ is the coordinate of object $\vec{p}_i$ in object group k in the X dimension;

$X_j$ is the coordinate of object $\vec{p}_j$ in object group k in the X dimension;

$Y_i$ is the coordinate of object $\vec{p}_i$ in object group k in the Y dimension;

$Y_j$ is the coordinate of object $\vec{p}_j$ in object group k in the Y dimension;

$\lambda$ is a normalizing constant;

correlation$_{ij}$ is the correlation between a defined neighborhood of object $\vec{p}_i$ and object $\vec{p}_j$;

$\gamma$ is a weight for the correlation term correlation$_{ij}$;

$I_i$ is a log intensity of object $\vec{p}_i$;

$I_j$ is a log intensity of object $\vec{p}_j$; and $\eta$ is a weight for $(I_i - I_j)^2$.

In some embodiments the optimization of the assignment of objects in the plurality of object groups is performed using a greedy search algorithm, a dynamic search, or a combination (e.g., hybrid) of a greedy search and a dynamic search. In some embodiments, an object in an object set in the plurality of object sets corresponds to a metabolite.

In some embodiments, the plurality of images are replicate spectra taken under a first experimental condition, the method further comprising using the plurality of object groups to combine the plurality of images into a single first average spectrum. In some embodiments, the method is repeated for a different second plurality of images, where the different second plurality of images are replicate spectra taken under a second experimental condition, the method further comprising using the plurality of object groups to combine the different second plurality of images into a single second average spectrum. In some embodiments the first experimental condition is absence of a perturbation (e.g., no exposure to siRNA or a drug) and the second experimental condition is presence of a perturbation (e.g., exposure to siRNA or a drug). In some embodiments, the alignment method is performed using the first average spectrum and the second average spectrum rather than replicates used to form the first average spectrum and the second average spectrum.

In some embodiments, the method further comprises outputting the plurality of object groups to a user interface device, a computer readable storage medium, a memory, or a local or remote computer system; or displaying the plurality of object groups. In some embodiments, the method further comprises aligning the plurality of images based upon object assignments within the plurality of the plurality of object groups. In some embodiments, the method further comprises outputting the plurality of aligned images to a user interface device, a computer readable storage medium, a memory, or a local or remote computer system; or displaying the plurality of aligned images.

Yet another embodiment provides an apparatus for aligning objects in a plurality of object sets. Each object set in the plurality of objects sets comprises the objects in a corresponding image in a plurality of images. The apparatus comprises a central processing unit and a memory that is coupled to the central processing unit. The memory comprises instructions for accessing the plurality of object sets. The memory further comprises an image comparison module for carrying out any of the above-described methods. For instance, in some embodiments, the image comparison module constructs, for each respective object in a first object set in the plurality of object sets, a corresponding object group that contains the respective object in the first object set, thereby constructing a plurality of object groups. Further, in such embodiments, the image comparison module computes, for each respective object in an object set in the plurality of object sets, a plurality of similarity metrics. Each similarity metric in the plurality of similarity metrics is between (i) the respective object and (ii) objects in an object group in the plurality of object groups. The respective object is added to a first object group in the plurality of object groups when (i) the similarity metric between the respective object and objects in the first object group is better than the similarity metric between the respective object and objects in any other object group in the plurality of object groups and (ii) the coordinate differences between the respective object and objects in the first object group are below threshold values. Otherwise, a new object group is added to the plurality of object groups and the respective object is added to the new object group. The image comparison module further comprises instructions for repeating the computing step for each remaining object set in the plurality of object sets. Objects that are in the same object group are deemed to correspond to each other. In some embodiments, the comparison module further comprises instructions for outputting the plurality of object groups to a user interface device, a computer readable storage medium, a memory, or a local or remote computer system; or displaying the plurality of object groups.

Still another aspect of the invention provides an apparatus for aligning objects in a plurality of object sets, where each object set in the plurality of objects sets comprises the objects in a corresponding image in a plurality of images. The apparatus comprises a central processing unit and a memory, coupled to the central processing unit. The memory comprises means for accessing the plurality of object sets, means for constructing, for each respective object in a first object set in the plurality of object sets, a corresponding object group that contains the respective object in the first object set, thereby constructing a plurality of object groups, and means for computing, for each respective object in an object set in the plurality of object sets, a plurality of similarity metrics, each similarity metric in the plurality of similarity metrics between (i) the respective object and (ii) objects in an object group in the plurality of object groups. The respective object is added to a first object group in the plurality of object groups when (i) the similarity metric between the respective object and objects in the first object group is better than the similarity metric between the respective object and objects in any other object group in the plurality of object groups and (ii) coordinate differences between the respective object and objects in the first object group are below threshold values. Otherwise, a new object group is added to the plurality of object groups and the respective object is added to the new object group. In some embodiments, the memory further comprises means for repeating such computations for each remaining object set in the plurality of object sets, where objects that are in the same object group are deemed to correspond to each other. In some embodiments, the memory further comprises means for outputting the plurality of object groups to a user interface device, a computer readable storage medium, a memory, or a local or remote computer system; or displaying the plurality of object groups.

Still another embodiment provides an apparatus for aligning objects in a plurality of object sets stored on a computer readable storage media. The storage media comprises a first plurality of binary values for accessing the plurality of object sets. The storage media comprises a second plurality of binary values for constructing, for each respective object in a first object set in the plurality of object sets, a corresponding object group that contains the respective object in the first object set, thereby constructing a plurality of object groups. The storage media comprises a third plurality of binary values for computing, for each respective object in an object set in the plurality of object sets, a plurality of similarity metrics, each similarity metric in the plurality of similarity metrics between (i) the respective object and (ii) objects in an object group in the plurality of object groups. The respective object is added to a first object group in the plurality of object groups when the similarity metric between the respective object and objects in the first object group is better than the similarity metric between the respective object and objects in any other object group in the plurality of object groups and (ii) coordinate differences between the respective object and objects in the first object group are below threshold values. Otherwise, a new object group is added to the plurality of object groups and the respective object is added to the plurality of object groups. The storage media comprises a fourth plurality of binary values for repeating the above-described computations for each remaining object set in the plurality of object sets, where objects that are in the same object group are deemed to correspond to each other. In some embodiments the computer readable storage media comprises a fifth plurality of binary values for outputting the plurality of object groups to a user interface device, a computer readable storage medium, a memory, or a local or remote computer system; or displaying the plurality of object groups.

Still another embodiment provides a method for aligning objects in a plurality of object sets. Each object set in the plurality of objects sets comprises a plurality of objects in a corresponding image in a plurality of images. Each of the objects in each of the plurality of objects sets are initially marked as untreated. The method comprises (A) constructing, for each respective object in a first object set in the plurality of object sets, a corresponding object group that contains the respective object in the first object set, thereby constructing a plurality of object groups. As described below, in typical embodiments, additional object groups are added to the plurality of object groups. The method further comprises (B) computing, for each respective untreated object in a target object set in the plurality of object sets, a similarity metric between a target object group in the plurality of object groups and the respective object, thereby computing a plurality of similarity metrics. The object in the target object set that has the best similarity score to the target object group is added to the target object group and marked as treated when the coordinate differences between the object and the target object group are below threshold values. Otherwise, a missing object is added to the target object group when the coordinate differences between the object and the target object group are not below threshold values. A missing object is a dummy object that imposes a penalty on the object group for inclusion of the dummy object. The method further comprises (C) repeating the computing step (B) for each remaining object set in the plurality of object sets thereby populating the target object group. The method further comprises (D) repeating the computing step (B) for each remaining respective object group in the plurality of objects groups, where the respective object group is designated as the target object group. In typical embodiments, the method further comprises steps (E) performing the method of (i) constructing an object group for an object in the plurality of objects sets that remains untreated, (ii) designating the object group the "target object group" and performing steps (B) and (C) for the target object group and (F) repeating step (E) until no untreated object remains in the plurality of object sets. It will be appreciated that a "missing object" will be added to each respective object group in the plurality of object groups that corresponds to an object set that does not contain an untreated object within threshold distances of a target object used in an instance of step (E) to construct an object group. Objects that are in the same object group are deemed to correspond to each other.

BRIEF DESCRIPTION OF THE DRAWINGS

FIG. 5 illustrates alternative alignment proposals that are evaluated using a greedy search algorithm in accordance with an aspect of the disclosed systems and methods.

Like reference numerals refer to corresponding parts throughout the several views of the drawings.

DETAILED DESCRIPTION

Figure 1:
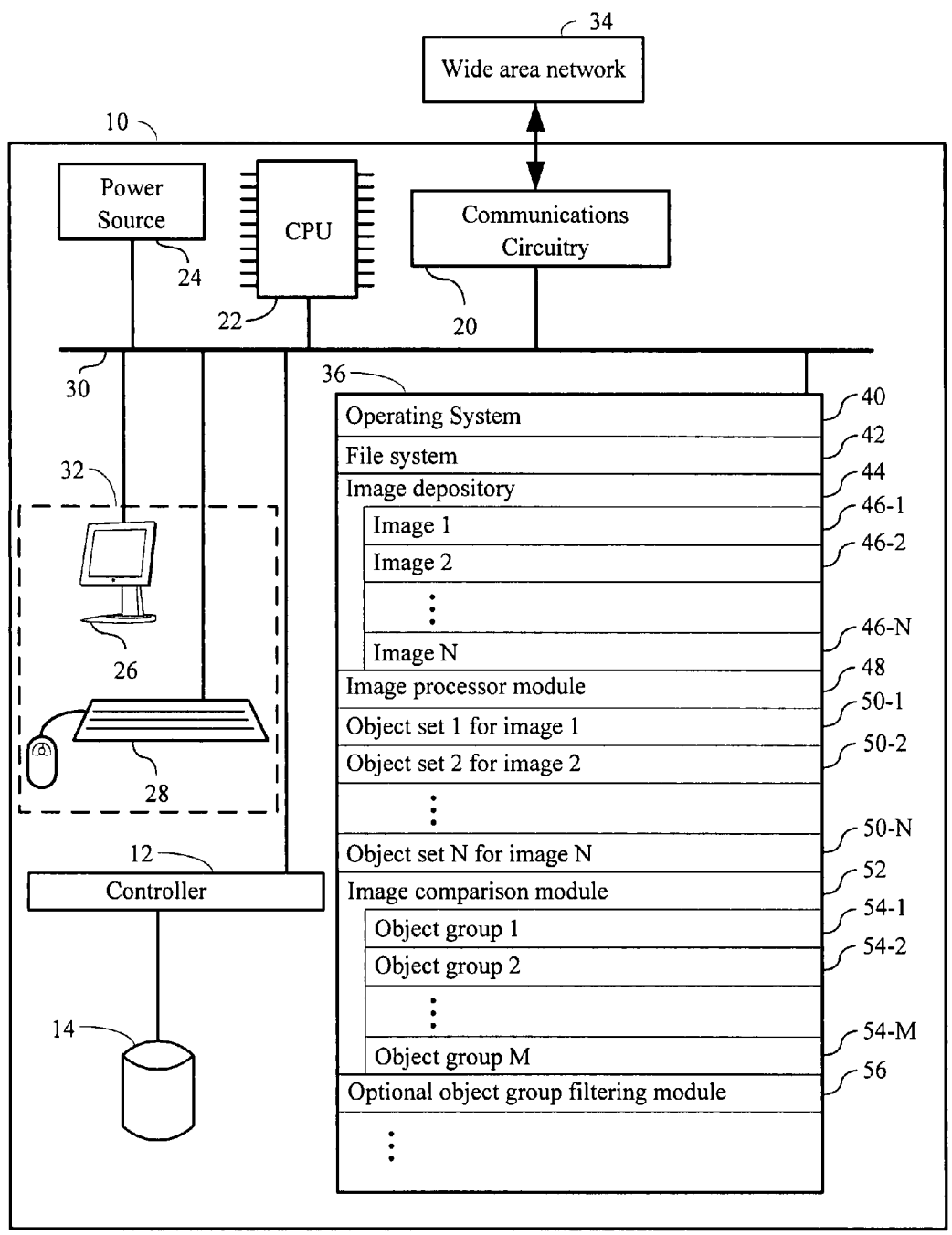
FIG. 1 illustrates an apparatus in accordance with an aspect of the disclosure.

FIG. 1 details an exemplary system for aligning objects in a plurality of object sets, each object set in the plurality of objects sets comprising the objects in a corresponding image in a plurality of images. The system is preferably a computer system 10 having:

a central processing unit 22;
a main non-volatile storage unit 14, for example, a hard disk drive, for storing software and data, the storage unit 14 controlled by storage controller 12;
a system memory 36, preferably high speed random-access memory (RAM), for storing system control programs, data, and application programs, comprising programs and data loaded from non-volatile storage unit 14; system memory 36 may also include read-only memory (ROM);
a user interface 32, comprising one or more input devices (e.g., keyboard 28) and a display 26 or other output device;
a network interface card or other communications circuitry 20 for connecting to any wired or wireless communication network 34 (e.g., a wide area network such as the Internet);
an internal bus 30 for interconnecting the aforementioned elements of the system; and
a power source 24 to power the aforementioned elements.

Operation of the computer 10 is controlled primarily by an operating system 40, which is executed by a central processing unit 22. Operating system 40 can be stored in system memory 36. In addition to an operating system 40, in a typical implementation, a system memory 36 includes:

a file system 42 for controlling access to the various files and data structures used by the disclosed systems and methods;
an image depository 44 comprising a plurality of images 46 (e.g., NMR spectra), in which each image 46 comprises objects (e.g., peaks or other features) that are to be aligned;
an image processor module 48 for analyzing images 46 and extracting, from each respective image 46, a corresponding object set 50 that contains a list of objects in the respective image 46;
an image comparison module 52 for aligning objects in the object sets 50;
a plurality of object groups 54, where each object group 54 is for a corresponding object that is present in all or some of the images 46; and
an optional group filtering module 56 for finding objects in the object group that satisfy one or more predetermined criteria.

As illustrated in FIG. 1, computer 10 comprises software program modules and data structures. The data structures stored in computer 10 include image depository 44, images 46, object sets 50, and object groups 54. Each of these data structures can comprise any form of data structure including, but not limited to, a flat ASCII or binary file, an Excel spreadsheet, a relational database (SQL), or an on-line analytical processing (OLAP) database (MDX and/or variants thereof).

In some embodiments, each of the aforementioned data structures is a single data structure. In other embodiments, such data structures in fact comprise a plurality of data structures (e.g., databases, files, archives) that may or may not all be hosted by the same computer 10. For example, in some embodiments, image depository 44 and the images 46 in the depository are stored either on computer 10 and/or on one or more computers that are addressable by computer 10 across wide area network or Internet 34. Thus, in some embodiments, any of the aforementioned data structures can be (i) stored on computer 10, (ii) stored on a combination of computer 10 and other computers (not illustrated in FIG. 1) that are addressable by computer 10 across, for example, wide area network 34, or (iii) are remotely stored in their entirety on one or more other computers (not illustrated in FIG. 1) that are addressable by computer 10 across, for example, wide area network or Internet 34.

As in the case of the data structures, it will be appreciated that many of the modules illustrated in FIG. 1 can also be located on one or more remote computers. For example, in some embodiments the disclosed methods are implemented as web service services. In such embodiments, image processor module 48, image comparison module 52 and/or object filtering module 56 can reside on a client computer that is in communication with computer 10 via network 34. In some embodiments, for example, image comparison module 52 can be an interactive web page.

In view of the foregoing, any arrangement of the data structures and software modules illustrated in FIG. 1 on one or more computers is within the scope of the present invention so long as these data structures and software modules are addressable with respect to each other across network 34 or by other electronic means. Thus, the present invention fully encompasses a broad array of computer systems.

Figure 3:
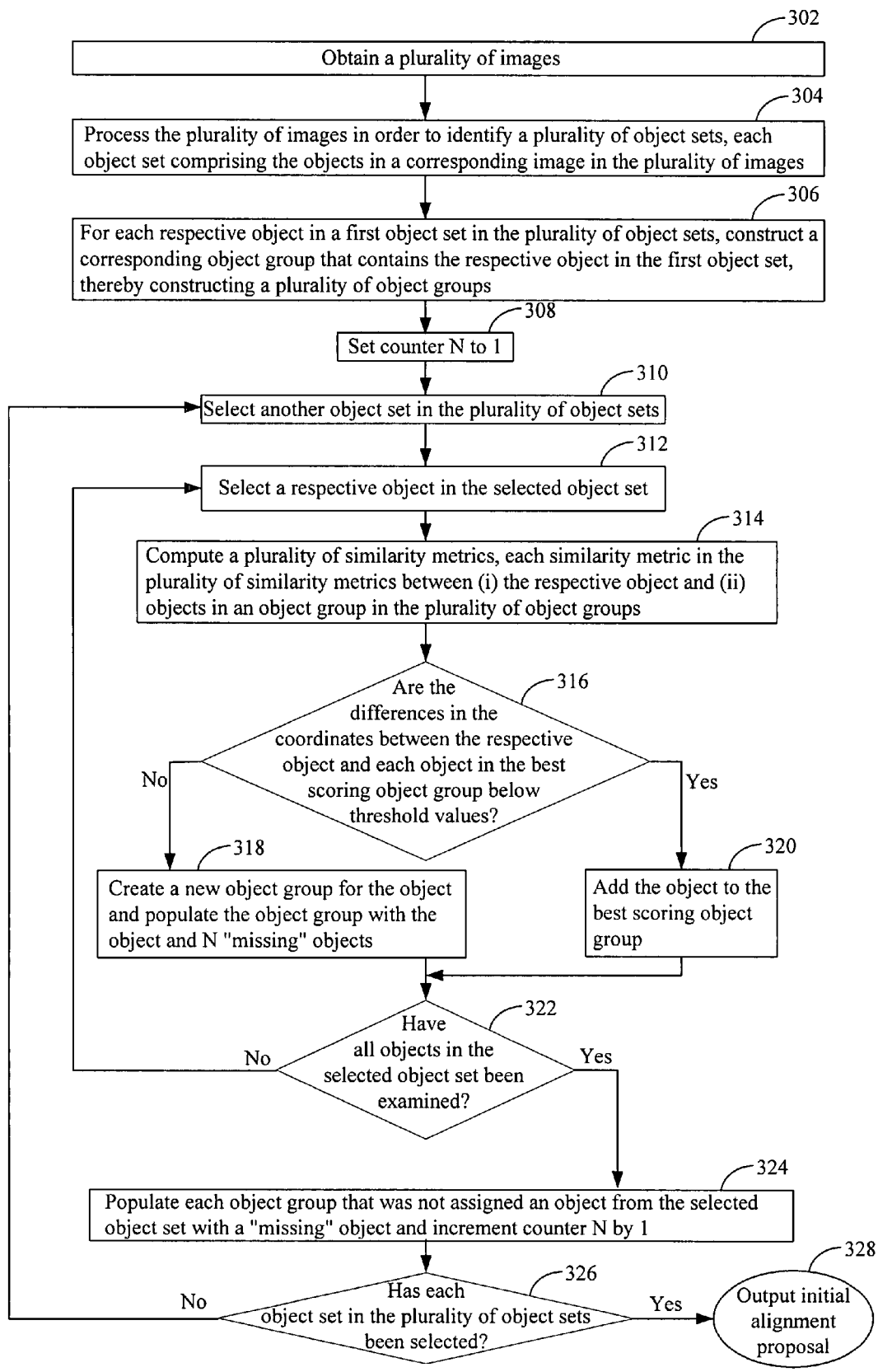
FIG. 3 illustrates one method for generating an initial alignment proposal in accordance with an aspect of the disclosure.

Exemplary computer systems have now been disclosed. Turning to FIG. 3, an exemplary process for aligning objects in images is disclosed.

Step 302. In step 302, a plurality of images 46 is obtained. Images 46 are any data structure that includes objects. In typical implementations, each image 46 will have a collection of objects, referred to herein as an object set 50. Moreover, typically, there is a correspondence between objects in one image 46 in the plurality of images and objects in other images 46 in the plurality of images. For example, in some embodiments, the images are nuclear magnetic resonance (NMR) images of samples taken from an organism at different time points, where individual objects in the images, peaks, represent metabolites in the samples. Thus, a first NMR image may have a peak for a first metabolite in a first biological sample and a second NMR image may have a peak for the very same first metabolite in a second biological sample. In such an example, the peak for the first metabolite in the first NMR image corresponds to the peak for the very same first metabolite in the second biological sample because both peaks represent the same metabolite. The problem presented in the art is that the coordinates of the peak for the first metabolite may shift from spectra to spectra because of a variety of factors including minor variations in the experimental conditions under which the spectra was measured, pH of the sample, etc.

In some embodiments, each image 46 in the plurality of images is a two-dimensional nuclear magnetic resonance (NMR) spectrum, a three-dimensional NMR spectrum, or a four-dimensional NMR spectrum and the objects in the plurality of images are peaks in the two-dimensional, three-dimensional, or four-dimensional NMR spectrum. In some embodiments, an image 46 in the plurality of images is a 2D nuclear Overhauser enhancement and exchange (NOESY) spectrum, a two-dimensional J-resolved (2D-J) spectrum, a homonuclear 2D correlated (COSY) spectrum, a 2D spin-echo correlated (SECSY) spectrum, a relayed coherence-transfer (RELAYED-COSY) spectrum, a $^1H$—$^{15}N$ COSY spectrum, a $^1H$—$^{31}P$ COSY spectrum, a $^{113}Cd$—$^1H$ COSY spectrum, a rotating-frame NOE (ROESY) spectrum, a total correlation (TOCSY) spectrum, a heteronuclear single quantum correlation (HSQC) spectrum, a heteronuclear multiple-quantum coherence (HMQC) spectrum, a heteronuclear multiple bond correlation (HMBC) spectrum, a two-dimensional heteronuclear correlation (HETCOR) spectrum, a double quantum filtered correlation (DQFC) spectrum, or a two-dimensional INADAQUATE spectrum.

The images 46 of the present invention are not, in fact, limited to "viewable" images. An image 46 within the scope of the present invention can be a dataset that comprises sufficient information to create a viewable image. For example, in the case of an NMR spectrum, an image 46 can be the data used to create the NMR spectrum rather than the NMR spectrum itself. Such data can be manipulated in the methods of the present invention as images 46 in the same manner as the NMR spectra itself.

In some embodiments, there are 2 or more images, 5 or more images, 10 or more images, or 100 or more images in the plurality of images to be aligned. In some embodiments, there are between 2 and 1000 images or less than 500 images to be aligned. In some embodiments, an image 46 is a one dimensional NMR spectrum, a two-dimensional NMR spectrum, a three-dimensional NMR spectrum, a four-dimensional NMR spectrum or the data that can be used to generate any of the aforementioned spectra. In some embodiments, an image 46 is a two-dimensional spectrum, or the data necessary to create the two-dimensional spectrum, obtained from a process other than NMR, including but not limited to, mass spectrometry, X-ray crystallography, an astronomical sky survey, and electrophoresis. In some embodiments, an image is an array of components of an emission or wave separated and arranged in the order of some varying characteristic such as wavelength, mass or energy. In some embodiments, the plurality of images obtained in step 302 is stored in the image depository 44 illustrated in FIG. 1.

In some embodiments, some images in the plurality of images represent measurements taken of a biological sample from one species whereas other images in the plurality of images represent measurements taken of a biological sample from another species. In some embodiments, some images in the plurality of images represent measurements taken of biological samples from organisms that have not been exposed to a perturbation whereas other images in the plurality of images represent measurements taken of biological samples from organisms that have been exposed to a perturbation. In some embodiments, some images in the plurality of images represent measurements taken of biological samples from organisms before they have been exposed to a perturbation whereas other images in the plurality of images represent measurements taken of biological samples from the same organisms after they have been exposed to a perturbation.

The perturbation can be environmental or genetic. Examples of environmental perturbations include, but are not limited to, exposure of an organism to a test compound, an allergen, pain, hot or cold temperatures. Additional examples of environmental perturbations include diet (e.g. a high fat diet or low fat diet), sleep deprivation, isolation, and quantifying a natural environmental influence (e.g., smoking, diet, exercise). Examples of genetic perturbations include, but are not limited to, the use of gene knockouts, introduction of an inhibitor of a predetermined gene or gene product, N-Ethyl-N-nitrosourea (ENU) mutagenesis, siRNA knockdown of a gene, or quantifying a trait exhibited by a plurality of members of a species.

In some embodiments, a perturbation is exposure to a drug or small molecule. Non-limiting examples of small molecules that can be used for such perturbations include, but are not limited to, those that satisfy the Lipinski's Rule of Five: (i) not more than five hydrogen bond donors (e.g., OH and NH groups), (ii) not more than ten hydrogen bond acceptors (e.g. N and O), (iii) a molecular weight under 500 Daltons, and (iv) a LogP under 5. The "Rule of Five" is so called because three of the four criteria involve the number five. See, Lipinski, 1997, Adv. Drug Del. Rev. 23, 3, which is hereby incorporated by reference herein in its entirety. In some embodiments, criteria in addition to Lipinski's Rule of Five are imposed. For example, in some embodiments, the small molecule has five or fewer aromatic rings, four or fewer aromatic rings, three or fewer aromatic rings, or two or fewer aromatic rings. In some embodiments, the small molecule is any organic compound having a molecular weight of less than 2000 Daltons.

Step 304. In step 304, the plurality of images are processed in order to identify a plurality of object sets 50, each object set 50 comprising the objects 200 in a corresponding image 46 in the plurality of images. In some embodiments, the plurality of images are NMR spectra and an object in an object set is a peak in an NMR spectrum from which the object set was obtained. In some embodiments, a peak is a local maximum within a predefined range in a NMR spectrum. In the case where the spectrum is a two-dimensional $^1H$—$^{13}C$ NMR spectrum, a peak can be, for example, a local maximum bounded by 0.03 parts per million (ppm) and 0.4 ppm for the proton and carbon dimension, respectively. Conventional processes can be used to obtain an object set from a corresponding image. For example, in embodiments where the image is a NMR spectrum, conventional programs such as Topspin (Bruker, Billerica, Mass.), VNMR (Varian, Palo Alto, Calif.), and NMRPipe (Delaglio et al., 1995, J. Biomol. NMR. 6, 277-293), each of which is hereby incorporated by reference herein, can be used to process the spectrum. Moreover, conventional spectral analysis programs such as the Sparky Assignment and Integration Software package (UCSF, San Francisco Calif.), ANSIG (Kraulis, 1989, J. Magn. Reson. 24, pp 627-633; Kraulis et al., 1994, Biochemistry 33, pp 3515-3531), NMR View (One Moon Scientific, Inc., Newark, N.J.), and XEASY (Bartels et al., 1995, Journal of Biomolecular NMR 6, 1-10), each of which is hereby incorporated by reference herein, can be used to assign peaks in a processed NMR spectrum to individual molecular constituents in a sample from which the spectrum was measured using techniques such as peak picking and support of sequence-specific resonance assignments, cross-peak assignments, cross-peak integration and rate constant determination for dynamic processes. In some embodiments, the foregoing processes are performed by image processor module 48 of computer 10 (FIG. 1).

Figure 6:
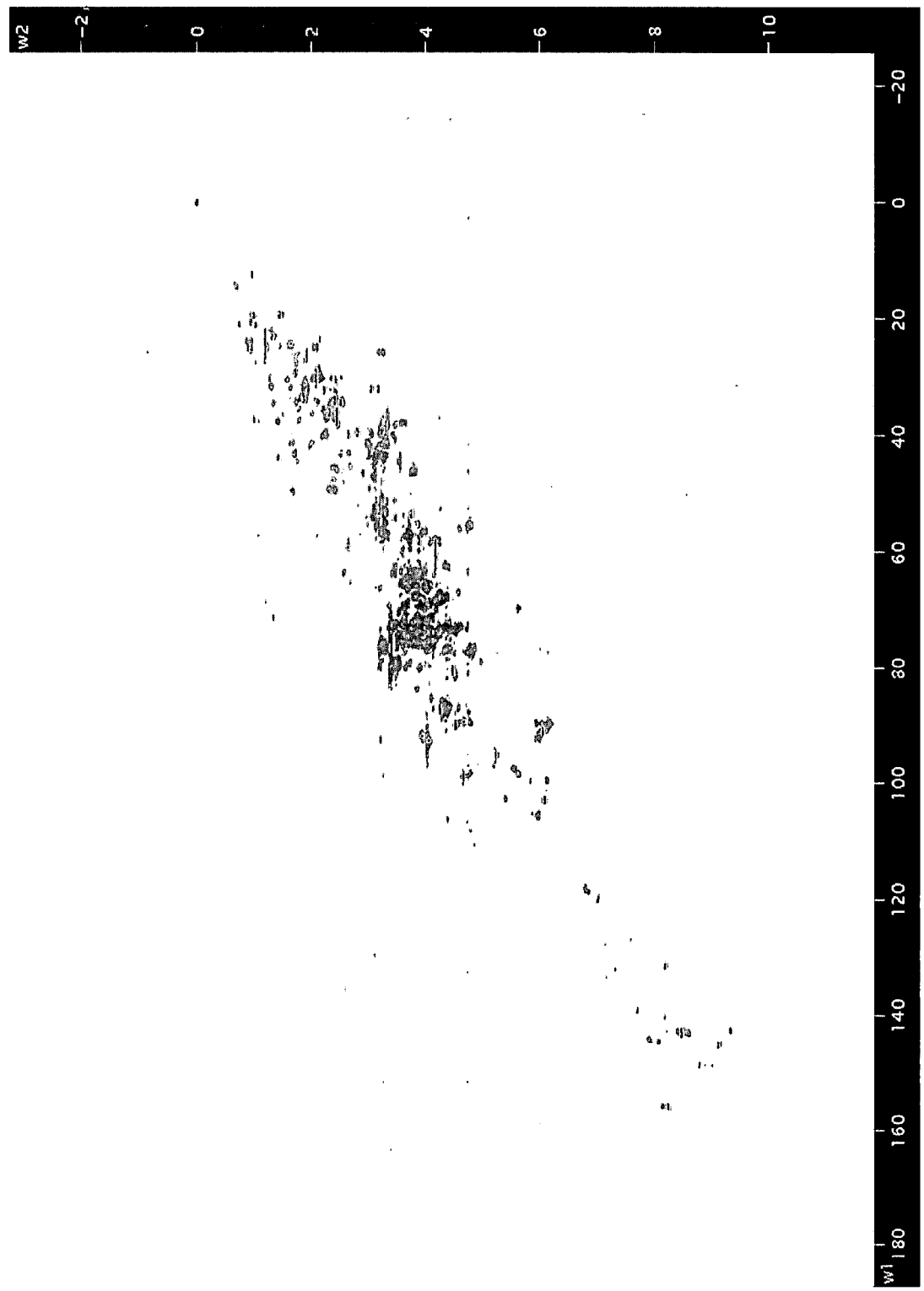
FIG. 6 is an exemplary image that is aligned with other images using the disclosed systems and methods.

In an example of the methods, consider the case in which three two-dimensional NMR spectra are taken from biological samples taken from a C57 mouse strain. Referring to FIG. 1, the three two-dimensional NMR spectra are examples of images 46. An example of one such two-dimensional NMR spectrum is illustrated in FIG. 6. Upon completion of steps 302 and 304, three object sets 50 will be created, each containing the peaks found in one of the three two-dimensional NMR spectra. Exemplary objects sets 50 for actual NMR spectra taken from three replicates of a biological sample are provided in Tables 1 through 3. In accordance with FIG. 6, in these tables, "w1" is the coordinate of the object (peak) in the NMR spectrum in the first dimension, "w2" is the coordinate of the object (peak) in the NMR spectrum in the second dimension, and "intensity" is the intensity of the object. Such intensities are used in some embodiments. In fact, the object sets for the actual NMR spectra contain many more objects that are not listed in the following tables.

TABLE 1

Object set for a first two-dimensional NMR spectrum

| w1 | w2 | intensity |
| --- | --- | --- |
| 51.8202 (670) | 3.20776 (629) | 728.739938 |
| 56.1198 (648) | 3.25998 (625) | 715.960651 |
| 56.7061 (645) | 3.22082 (628) | 594.922013 |
| 63.5463 (610) | 3.8866 (577) | 528.789563 |
| 72.5363 (564) | 3.39053 (615) | 501.989851 |
| 63.5463 (610) | 3.71689 (590) | 493.036187 |
| 66.087 (597) | 4.00409 (568) | 476.160778 |
| 38.3352 (739) | 3.3122 (621) | 462.246448 |
| 57.2924 (642) | 3.69078 (592) | 446.185508 |
| 53.7746 (660) | 3.12944 (635) | 436.300304 |
| 79.3765 (529) | 3.39053 (615) | 415.757730 |
| 92.2752 (463) | 4.0302 (566) | 402.909618 |
| 46.1526 (699) | 3.76911 (586) | 362.580631 |
| 89.7345 (476) | 6.11894 (406) | 362.220957 |
| 54.9472 (654) | 3.25998 (625) | 352.381942 |
| 75.6633 (548) | 3.19471 (630) | 346.322361 |
| 73.318 (560) | 4.50017 (530) | 320.788939 |
| 78.7902 (532) | 3.46886 (609) | 299.606817 |
| 79.3765 (529) | 3.48191 (608) | 286.014891 |
| 77.2267 (540) | 4.78737 (508) | 285.716954 |

TABLE 2

Object set for a second two-dimensional NMR spectrum

| w1 | w2 | intensity |
| --- | --- | --- |
| 52.3218 (668) | 3.19261 (631) | 743.813993 |
| 56.8168 (645) | 3.23178 (628) | 695.304989 |
| 63.657 (610) | 3.89756 (577) | 670.259825 |
| 63.657 (610) | 3.72785 (590) | 638.737466 |
| 72.647 (564) | 3.40149 (615) | 636.052566 |
| 53.8853 (660) | 3.1404 (635) | 627.377496 |
| 92.3859 (463) | 4.04116 (566) | 600.827085 |
| 79.4872 (529) | 3.40149 (615) | 589.767890 |
| 75.774 (548) | 3.21872 (629) | 521.271566 |
| 56.2305 (648) | 3.27094 (625) | 498.680607 |
| 66.1977 (597) | 4.01505 (568) | 489.310996 |
| 38.6414 (738) | 3.29705 (623) | 461.543027 |
| 79.4872 (529) | 3.49287 (608) | 430.253000 |
| 46.2633 (699) | 3.78007 (586) | 388.366533 |
| 89.8452 (476) | 6.14296 (405) | 373.252446 |
| 55.0579 (654) | 3.27094 (625) | 361.924107 |
| 73.4287 (560) | 4.51113 (530) | 338.047962 |
| 57.2077 (643) | 3.66258 (595) | 331.262085 |
| 77.3374 (540) | 4.79833 (508) | 302.465531 |
| 55.4488 (652) | 4.75917 (511) | 286.376034 |

TABLE 3

Object set for a third two-dimensional NMR spectrum

| w1 | w2 | intensity |
| --- | --- | --- |
| 50.7063 (676) | 3.25083 (627) | 1273.478624 |
| 38.1985 (740) | 3.39443 (616) | 881.742160 |
| 57.1557 (643) | 3.74691 (589) | 710.135319 |
| 56.7648 (645) | 3.22472 (629) | 703.270792 |
| 72.3996 (565) | 3.40749 (615) | 700.766781 |
| 78.6535 (533) | 3.48582 (609) | 639.906221 |
| 56.1785 (648) | 3.26389 (626) | 568.174912 |
| 63.605 (610) | 3.73385 (590) | 556.711390 |
| 63.605 (610) | 3.90356 (577) | 553.028188 |
| 98.7832 (430) | 4.64768 (520) | 550.376595 |
| 66.1457 (597) | 4.008 (569) | 506.933668 |
| 76.8946 (542) | 3.25083 (627) | 488.875372 |
| 94.8745 (450) | 5.23513 (475) | 399.728237 |
| 89.7932 (476) | 6.12285 (407) | 390.148245 |
| 73.3767 (560) | 4.50407 (531) | 380.323277 |
| 74.1585 (556) | 3.53803 (605) | 369.794459 |
| 39.762 (732) | 2.24563 (704) | 366.979890 |
| 46.2113 (699) | 3.77302 (587) | 353.997640 |
| 74.1585 (556) | 3.83829 (582) | 340.005184 |
| 55.0059 (654) | 3.27694 (625) | 336.948278 |

The steps described below use the object sets, such as those illustrated in Tables 1-3, to align the objects and, ultimately, in some embodiments, the images from which the object sets were extracted.

Upon completion of step 304, a plurality of object sets, one for each image in the plurality of images, is created. However, conventional processes described above do not provide satisfactory alignment proposals that align the objects in one object set 50 to the objects in another object set 50. Since each object set 50 represents an image 46, such conventional processes described above do not provide satisfactory alignment proposals that align images 46 onto each other.

An alignment proposal is a proposal to assign correspondence object pairs for a set of images: if a pair of objects is proposed to represent the same observable (e.g., a pair of peaks in two different NMR spectra is proposed to represent the same metabolite in two different biological samples), this pair of objects is deemed to be corresponding (and are therefore aligned). An alignment proposal follows two rules. First, the "corresponding" assignment is transitive: if object 1 and object 2 are corresponding and object 1 and object 3 are corresponding, than object 2 and object 3 are corresponding. Second, if a pair of objects consists of two different objects from the same image 46, than they are deemed to be non-corresponding, because within a single image 46 different objects are considered to represent different observables (e.g., different metabolites).

Figure 7:
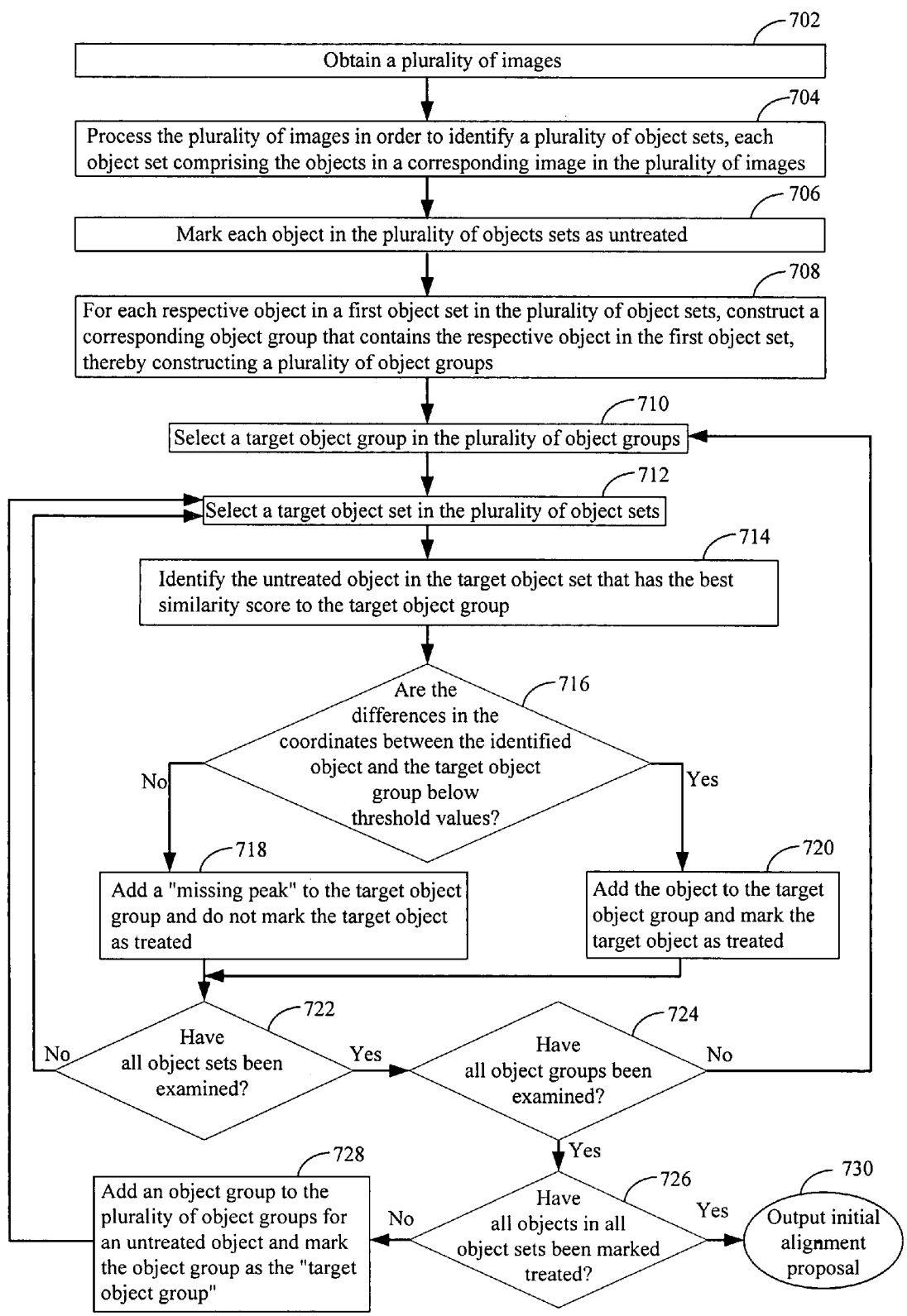
FIG. 7 illustrates another method for generating an initial alignment proposal in accordance with an aspect of the disclosure.

The alignment proposal rules imply that any object 200 in an image 46 cannot be deemed to be corresponding (aligned) to two objects in another image. It is clear that an object is always corresponding to itself and, furthermore, that if object 1 corresponds to object 2, than object 2 corresponds to object 1. Therefore, mathematically, this corresponding assignment can be viewed as an equivalence assignment. The remaining steps illustrated in FIG. 3 describe methods for producing an initial alignment proposal. The steps illustrated in FIG. 4 describe methods for refining the alignment proposal. FIG. 7 illustrates an alternative method for producing an initial alignment proposal which can then be refined using, for example, the method illustrated in FIG. 4. The steps illustrated in FIGS. 3, 4, and 7 or logical equivalents or combinations of such steps, are performed by image comparison module 52 in some embodiments.

Step 306. In step 306 object groups are constructed. An object group is the set of all objects assigned to the same observable (e.g. a metabolite or other compound, etc.) by an alignment proposal. An object group satisfies two rules. First, if two objects are deemed to be "corresponding," they are in the same object group. Second, any two objects in the same object group are deemed to be "corresponding." Therefore, given this and the rules regarding alignment proposals above, each object in and object group must be from a different image.

Step 306 begins by selecting an object set, referred to as the first object set, in the plurality of object sets. This first object set contains the objects in an image in the plurality of images. Any object set in the plurality of object sets, and hence, any image in the plurality images, can be selected. Next, an object group is created for each object in the first object set. So, if the object set, corresponding to an image in the plurality of images, contains 50 objects, 50 object groups are created. For example, if the image corresponding to the first object set is an NMR spectrum, than the objects in the object set are peaks and an object group is created for each peak in the NMR spectrum. If there are fifty peaks in the NMR spectrum corresponding to the first object set, than fifty object groups are created, one for each peak.

The net result of step 306 is the formation of a plurality of object groups. At the end of step 306, there is an object group for each object in a selected single first object set in the plurality of object sets. Each object group, at this stage, contains exactly one object from the selected first object set.

Step 308. In subsequent steps, objects in each of the remaining object sets are examined in order to assign them to object groups. In preferred embodiments, each object group contains the same number of objects. Thus, for illustrative purposes, a counter is used in the process illustrated in FIG. 3 as a way of making sure that each object group contains the same number of objects. In step 308, this counter is set to 1 because each existing object group presently contains one object.

Step 310. In step 310, another object set is selected. The object set selected in step 310 is any object set that has not previously been selected for examination. The first time step 310 is run (i.e., the first instance of step 310), only one object set has been examined, the first object set described in step 306. However, as the algorithm proceeds and step 310 is repeated (i.e., subsequent instances of step 310), than care is preferably taken to make sure that an object set that has not previously been examined by the process of step 310 is selected in each new instance of step 310.

Step 312. Step 312 is the beginning of a loop that ends with step 322. Loop 312-322 is performed in order to examine all the objects in the object set selected in the last instance of step 310. In step 312, a respective object is selected in this object set. As step 312 is repeated (i.e., successive instances of step 312), step 312 selects an object from the object set that had not previously been selected from the object set in a previous instance of step 312.

Step 314. Step 314 determines which object group to place the object picked in the last instance of step 312. This is accomplished by computing a plurality of similarity metrics. Each similarity metric is between (i) the respective object picked in the last instance of step 312 and (ii) objects in an object group in the plurality of object groups. So, if there are fifty object groups, fifty similarity metrics will be computed. Each similarity metric will be between the object to be assigned (picked in the last instance of step 312) and the objects in an object group in the plurality of object groups.

Consider the case in which an object group contains one object $\vec{p}_j$. One way to compute the similarity metric between the object $\vec{p}_j$ in the object group and the respective object picked in the last instance of step 312, denoted $\vec{p}_i$, is to compute the negative square of the Euclidean distance between $\vec{p}_i$ and $\vec{p}_j$:

$$\text{sim}(\vec{p}_i, \vec{p}_j) = -\{\text{dist}(\vec{p}_i, \vec{p}_j)\}^2.$$

Consider the case in which an object group contains multiple objects $P = \{\vec{p}_1, \ldots, \vec{p}_J\}$. One way to compute the similarity metric between the objects P in the object group and the respective object $\vec{p}_i$ picked in the last instance of step 312 is to compute the negative square of the Euclidean distance between $\vec{p}_i$ and P:

$$\text{sim}(\vec{p}_i, P) = -\sum_{j=1}^{J} \{\text{dist}(\vec{p}_i, \vec{p}_j)\}^2.$$

In alternative embodiments, metrics other than Euclidean distance can be used to compute $\text{sim}(\vec{p}_i, P)$, such as a Manhattan distance, a Chebychev distance, an angle between vectors, a correlation distance, a standardized Euclidean distance, a Mahalanobis distance, a squared Pearson correlation coefficient, or a Minkowski distance. Such metrics can be computed, for example, using SAS (Statistics Analysis Systems Institute, Cary, N.C.) or S-Plus (Statistical Sciences, Inc., Seattle, Wash.). Such metrics are described in Draghici, 2003, *Data Analysis Tools for DNA Microarrays*, Chapman & Hall, CRC Press London, chapter 11, which is hereby incorporated by reference herein in its entirety for such purpose.

The exact formulation of the similarity metric will depend on the characteristics of the images that are being aligned. For example, consider the case where the images are two-dimensional $^1H$—$^{13}C$ NMR. In such instances, a similarity metric based upon a Euclidean distance can be constructed as:

$$\text{sim}(\vec{p}_i, P) = -\sum_{j=1}^{J} \{\text{dist}(\vec{p}_i, \vec{p}_j)\}^2 = \sum_{j} -\{(C_i - C_j)^2 + \lambda(H_i - H_j)^2\}$$

Because the scales of the carbon and proton dimensions are different, a normalizing constant λ is multiplied to the coordinates $(H_i-H_j)^2$ in the proton dimension to make the distance measure unbiased.

Step 316. In step 316, a determination is made as to which object group achieved the best scoring similarity metric. In some embodiments, particularly those that use the negative Euclidean distance described above, the best scoring similarity metric is the similarity metric that most closely approaches zero. A check is made to determine whether the differences in the coordinates between the respective object that is being assigned to an object group, $\vec{p}_i$, and each object in the best scoring object group are below threshold values. For instance, consider the case in which the best scoring object group contains a single object, $\vec{p}_j$. Further suppose that the object is characterized by a first dimension value X and a second dimension value Y. Here, the coordinate differences between the respective object $\vec{p}_i$ and an object in the best scoring object group is below threshold values when $|X^2-X^1|<T_1$, and $|Y^2-Y^1|<T_2$ where
- $X^2$ is the first dimension indicator for the respective object $\vec{p}_i$;
- $X^1$ is the first dimension indicator for the object $\vec{p}_j$ in the best scoring object group;
- $Y_2$ is the second dimension indicator for the respective object $\vec{p}_i$;
- $Y_1$ is the second dimension indicator for the object $\vec{p}_j$ in the best scoring object group;
- $T_1$ is the first dimension threshold limit; and
- $T_2$ is the second dimension threshold limit.

If either distance test fails, the respective object $\vec{p}_i$ is not added to the best scoring object group. In one example, the plurality of images are two-dimensional $^1H$—$^{13}C$ NMR images and the first dimension value X is for carbon (C) and the second dimension value Y is for hydrogen (H), and the coordinate differences between the respective object $\vec{p}_i$ and an object $\vec{p}_j$ in the best scoring object group is below threshold values when $|C^2-C^1|<B_C$, and $|H^2-H^1|<B_H$ where
- $C^2$ is the first dimension indicator for the respective object $\vec{p}_i$;
- $C^1$ is the first dimension indicator for the object $\vec{p}_j$ in the best scoring object group;
- $H^2$ is the second dimension indicator for the respective object $\vec{p}_i$;
- $H^1$ is the second dimension indicator for the object $\vec{p}_j$ in the best scoring object group;
- $B_C$ is the first dimension threshold limit; and
- $B_H$ is the second dimension threshold limit.

In some embodiments, $B_C$ is 10 parts per million (PPM) or less, 9 PPM or less, 8 PPM or less, 7 PPM or less, 6 PPM or less, 5 PPM or less, 4 PPM or less, 3 PPM or less, 2 PPM or less, 1 PPM or lees, or 0.5 PPM or less. In some embodiments $B_H$ is 10 parts per million (PPM) or less, 9 PPM or less, 8 PPM or less, 7 PPM or less, 6 PPM or less, 5 PPM or less, 4 PPM or less, 3 PPM or less, 2 PPM or less, 1 PPM or lees, or 0.5 PPM or less.

In some embodiments each image in the plurality of images is an N-dimensional image, where N is 1, 2, 3, 4, 5, 6, 7, 9, 10 or greater than 10. In such embodiments a coordinate difference between the respective object $\vec{p}_i$ and an object in the best scoring object group is below threshold values when $|C_1^2-C_1^1|<B_1$, $|C_2^2-C_2^1|<B_2$

...

$|C_N^2-C_N^1|<B_N$ where
- $C_i^2$ is the $i^{th}$ dimension indicator for the respective object $\vec{p}_i$;
- $C_i^1$ is the $i^{th}$ dimension indicator for the object in the best scoring object group; and
- $B_i$ is the $i^{th}$ dimension threshold limit.

If any of these N distance test fail, the respective object $\vec{p}_i$ is not added to the best scoring object group.

The examples for determining whether the coordinates of the respective object $\vec{p}_i$ and the coordinates of objects in the best scoring object group are below threshold values given above do not address the case in which an object group contains multiple objects. There are two different ways that such a case can be addressed. In one approach, the coordinates of all the objects in the object group are averaged together to form an object $\vec{p}_j$ that represents the average values of all the objects in the object group. The distance test is then performed between the respective object $\vec{p}_i$ and the averaged object $\vec{p}_j$. In another approach, separate distance tests given above are performed between the respective object $\vec{p}_i$ and each object in the best scoring object group. If any of these distance tests fail, the respective object $\vec{p}_i$ is not added to the best scoring object group.

Step 318. If the distance rules between the respective object $\vec{p}_i$ and the objects in the best scoring object group are not satisfied (316-No), than a new object group for the respective object $\vec{p}_i$ is created and the respective object $\vec{p}_i$ is placed in the object group. When the counter N equals one and loop 312-322 has been completed for all of the objects in the object set selected in the last instance of step 310, the maximum number of objects that can be in any given object group will be two at this stage. However, some object groups will only contain one object if step 318 is performed in any iteration of loop 312-322 (and N equals one). Thus, to help ensure that each object group contains the same number of objects, "missing objects" are added to the object groups 54 created by step 318. For example, when N=1, one "missing object" is added to the object groups 54 created by step 318 so that each object group 54 created by step 318 has two objects: one object from the object set selected in the last instance of step 310 and one "missing object." A missing object is a dummy object that has the properties:

sim(missing object, real object)=sim(real object, missing object), sim(missing object, real object)=a predetermined missing penalty, sim(real object, missing object)=a predetermined missing penalty, and sim(missing object, missing object)=a predetermined missing penalty.

The value of the predetermined missing property is application dependent and is chosen to penalize the introduction of missing objects into the object groups.

When loop 312-324 has been repeated a number of times, so that N is larger, a larger number of "missing objects" are added to object groups 54 created in instances of step 318. For example, when an object group 54 is created by step 318 when N is 5, five "missing objects" (dummy or null objects) are added to the object group 54 so that the object group has a total of six objects, one object from the object set selected in the last instance of step 310 and five "missing objects."

Step 320. If the distance rules between the respective object $\vec{p}_i$ and the objects in the best scoring object group 54 are satisfied (316-Yes), than the respective object $\vec{p}_i$ is placed in the object group 54. However, only one object from any given object set 50 is placed into a given object group 54. Therefore, if an object from the object set selected in the last instance of step 310 has already been placed in a particular object group 54, the similarity value between the respective object $\vec{p}_i$ and objects in the particular object group is either ignored or is not computed in order to ensure that the particular object group 54 cannot be deemed to be the best scoring object group. In this way, only one object from any given object set 50 is placed into a given object group 54.

Step 322. In step 322 a determination is made as to whether all objects in the object set 50 selected in the last instance of step 310 have been assigned to object groups 54. If not (322-No), process control returns to step 312 and loop 312-322 is repeated for another object in the object set 50 selected in the last instance of step 310. Process control passes on to step 324 when all objects in the object set 50 selected in the last instance of step 310 have been assigned to object groups 54 (322-Yes).

Step 324. Step 324 is reached when all the objects in a selected object set 50 have been assigned to object groups. In preferred embodiments, the alignment proposals computed herein rely on object groups 54 that each contains the same number of objects. However, the process described above, including loop 312-322, does not ensure that each object group 54 contains the same number of objects. For example, an object group 54 could be created in step 306 that is not populated by an object in each iteration of loop 312-322. Thus, in step 324, each object group 54 that was not assigned an object from the object set selected in the last instance of step 310 is assigned a "missing" object. Of course, there are other ways to ensure that object groups 54 are rounded up using "missing" (dummy) objects so that each object group 54 has the same number of objects. The methods described here, including the use of a counter, merely serve to illustrate one of many ways that a plurality of object groups 54, each have the same number of objects can be created by back-filling object groups 54 that have less than the maximum number of objects with dummy "missing" objects. In an alternative approach, rather than using a counter and adding dummy "missing" objects in instances of step 318 and 324, such dummy "missing" objects could be added just prior to creation of the initial alignment proposal after all of the object sets 54 have been examined. In this alternative approach, the object groups 54 are examined to determine the maximum number of objects contained in any one object group. The object groups 54 that do not have this maximum number of objects are back-filled with dummy "missing" objects until they do have the maximum number of objects.

Steps 326 and 328. In step 326, a determination is made as to whether each object set 54 in the plurality of object sets has been examined by an iteration of loop 310-324. If not (326-No), process control returns to step 310 where another object set 50 in the plurality of object sets 50 is selected and loop 310-324 is repeated for the new object set. If each object set 54 in the plurality of object sets has been examined by an iteration of loop 310-324 (326-Yes), the initial alignment proposal comprising the plurality of object groups is outputted (step 328). In some embodiments, this outputting step merely means that the object groups 54 are stored, however transiently, in memory 36 and/or data storage 14, or in some other memory that is accessible by computer 10 across wide area network 34 or some other form of network. In some embodiments, the plurality of object groups are outputted to a user interface device, a computer readable storage medium, a memory, or a local or remote computer system; or the plurality of object groups are displayed.

Figure 2:
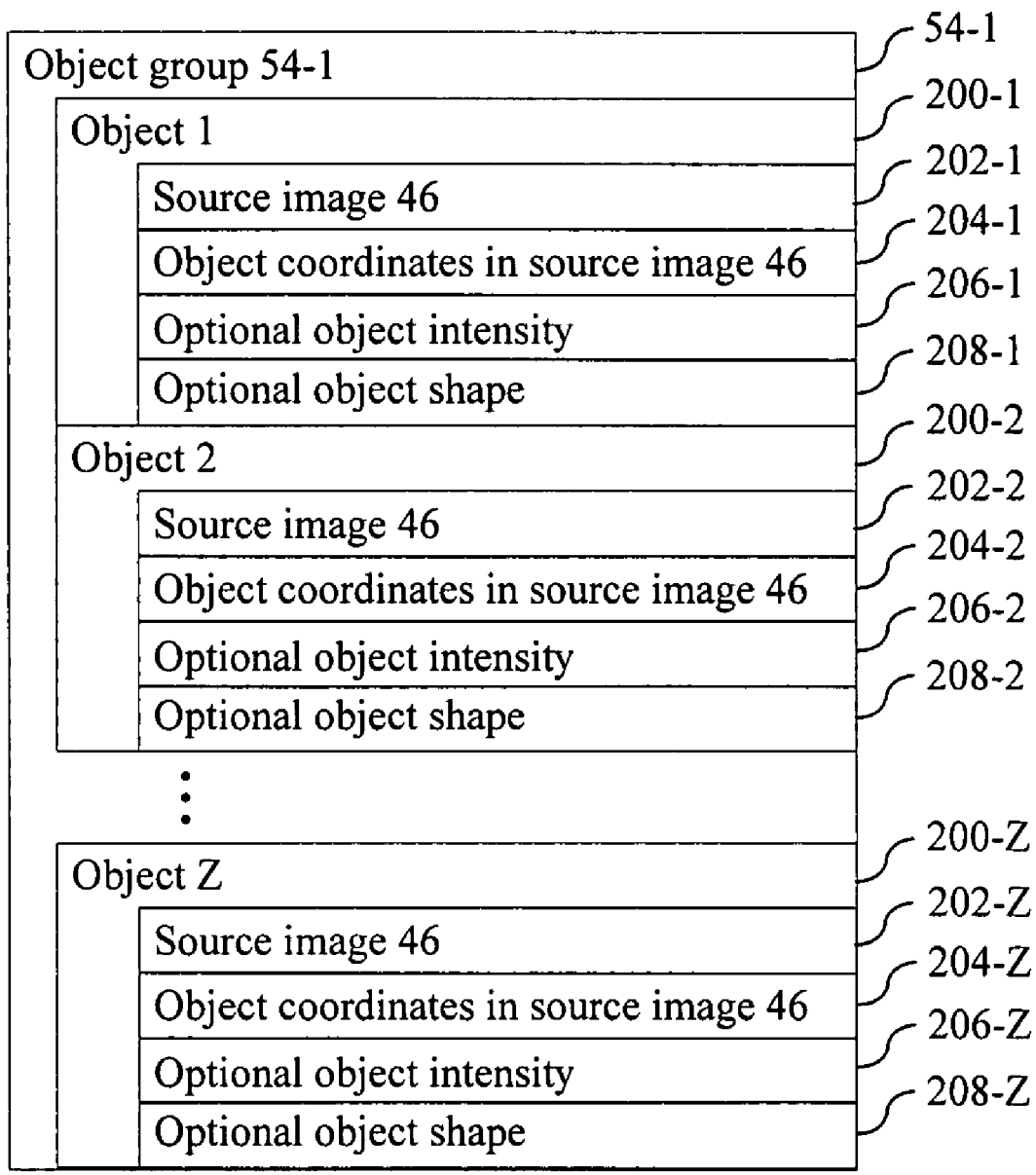
FIG. 2 illustrates an object group data structure in accordance with an aspect of the disclosure.

In some embodiments, the initial alignment proposal is stored in memory 36 as a plurality of object groups 54. In some embodiments, each object group 54 represents one observable that is measured in a sample and manifests itself as an object in the plurality of images. For example, in some embodiments, each object group 54 represents a metabolite that is present in some or all of a set of biological samples from which the plurality of images were measured. Turning to FIG. 2, additional detail for an object group 54 in accordance with one embodiment is illustrated. Upon completion of the process illustrated in FIG. 3, the exemplary object group 54 will contain a plurality of objects 200. Each object 200 in the object group 54 is from a different object set 50 and, hence, from a different image 46 in the plurality of images. Each object 200 in an object set 54 should represent the same observable. For example, if object 200-1 is a peak that represents a measurement of a particular metabolite in a first image 46, than objects 200-2 through 200-Z should each be a peak that represents a measurement of the same metabolite in other images 46.

As illustrated in FIG. 2, in some embodiments, an object group 54 stores particular information about each object 200 in the object group including, for example, the source image 46 from which the object 200 was found, the coordinates 204 of the center, effective center, or maximal part of the object in the source image, an optional object intensity 206 in the image and, optionally, one or more characteristics that provide a quantification 208 of the object shape 208 in the image.

The process illustrated in FIG. 3 generates an initial alignment proposal which comprises a plurality of object groups 54. As illustrated in FIG. 2, each of the object groups 54, upon completion of the process illustrated in FIG. 2, comprises a plurality of objects 200 from different images 46. Each such object 200 in a given object group 54 should represent the same observable in measured data. When objects 200 in an object group 54 do represent the same observable in measured data, the objects 200 are said to "correspond" to each other. If a first object 200 in a particular object group 54 does not represent the same observable (e.g., metabolite) as a second object in the particular object group, the first and second object do not correspond to each other and one of the objects should be removed from the object group 54.

If the images represent NMR measurements of metabolites in samples, each object 200 in a given object group 54 in an alignment proposal could be an NMR spectral peak generated by the same metabolite. This NMR spectral peak could be present in each image of a biological sample in which the given metabolite is found.

Referring to FIG. 7, an alternative method for generating an initial alignment proposal is provided. Steps 702 and 704 are performed in the same manner as steps 302 and 304 of FIG. 3, respectively. In step 706 each of the objects in each of the object sets 50 is marked as untreated.

Step 708. In step 708, a first object set 50 in the plurality of objects sets is selected and, for each respective object in the first object set 50, an object group 54 that contains the respective object is constructed, thereby constructing a plurality of object groups 54. For example, consider the case where there are 100 object sets 50. A first object set 50 is selected from among the 100 object sets 50. Say that the first object set 50 contains 50 objects. For each respective object in the 50 objects in the first object set 50, an object group 54 is created that contains the respective object.

Step 710. In step 710 a target object group 54 in the plurality of object groups 54 is selected. In the example above where the first object set 50 contains 50 objects, step 710 entails selecting one of the 50 object groups 54 that was created in step 708.

Step 712. In step 712, a target object set 50 in the plurality of object sets 50 identified in step 704 is selected.

Step 714. In step 714, an untreated object in the target object set 50 selected in the last instance of step 712 that has the best similarity score to the target object group 54 selected in the last instance of step 710 is selected. In the first iteration of loop 714-722 for a given target object group 54, the target object group 54 will only contain the object from the first object set 50. Thus, in the first instance of step 714 for a given target object group 54, step 714 involves determining the similarity between the single object in the target object group 54 and each untreated object in the target object set 50. However, step 714 is repeated for each target object set 50 in the plurality of target object sets 50. Suppose that currently n−1 object sets 50 have been processed by loop 714-722 and, therefore, the target object group 54 has n−1 objects, either real objects or "missing" objects: $P=\{\vec{p}_1, \vec{p}_2, \ldots, \vec{p}_{n-1}\}$. Then an $n^{th}$ object set 50 is selected in step 712 and the object $\vec{p}_n$ in this $n^{th}$ target object set 50 that is still untreated and has the largest (best) similarity to the target object group P is identified. For any object $\vec{p}$ in the $n^{th}$ object set 50, $$\text{sim}(\vec{p}, P) = \sum_{i=1}^{n-1} \text{sim}(\vec{p}, \vec{p}_i),$$

where $\vec{p}_i$ is in the set $\{\vec{p}_1, \vec{p}_2, \ldots, \vec{p}_{n-1}\}$.

Steps 716-720. In step 716, a determination is made as to whether the untreated object $\vec{p}_n$ in the target object set 50 that has the best similarity score to the target object group P that was identified in step 714 are compatible. For instance, consider the case in which the target object group contains a single object, $\vec{p}_j$. Further suppose that $\vec{p}_j$ is characterized by a first dimension value X and a second dimension value Y. Here, the coordinate differences between the untreated object identified in step 714 $\vec{p}_i$ and the target object group are below threshold values when $|X^2 - X^1| < T_1$, and $|Y^2 - Y^1| < T_2$ where
$X^2$ is the first dimension indicator for the untreated object $\vec{p}_i$;
$X^1$ is the first dimension indicator for the object $\vec{p}_j$ in the target object group;
$Y_2$ is the second dimension indicator for the untreated object $\vec{p}_i$;
$Y_1$ is the second dimension indicator for the object $\vec{p}_j$ in the target object group;
$T_1$ is the first dimension threshold limit; and
$T_2$ is the second dimension threshold limit.

If either distance test fails (716-No), the untreated object $\vec{p}_i$ is not added to the target object group 54, but rather, a "missing peak" is added to the target object group 54 (step 718). If both distance tests are satisfied (716-Yes), than the untreated object $\vec{p}_i$ is added to the target object group 54 (step 720) and the untreated object $\vec{p}_i$ is marked as treated.

In one example, the plurality of images are two-dimensional $^1$H—$^{13}$C NMR images and the first dimension value X is for carbon (C) and the second dimension value Y is for hydrogen (H), and the coordinate differences between the untreated object $\vec{p}_i$ identified in step 714 and the target object group $\vec{p}_j$ is below threshold values when $|C^2 - C^1| < B_C$, and $|H^2 - H^1| < B_H$ where
$C^2$ is the first dimension indicator for the untreated object $\vec{p}_i$;
$C^1$ is the first dimension indicator for the object $\vec{p}_j$ in the target object group;
$H^2$ is the second dimension indicator for the untreated object $\vec{p}_i$;
$H^1$ is the second dimension indicator for the object $\vec{p}_j$ in the target object group;
$B_C$ is the first dimension threshold limit; and
$B_H$ is the second dimension threshold limit.

In some embodiments, $B_C$ is 10 parts per million (PPM) or less, 9 PPM or less, 8 PPM or less, 7 PPM or less, 6 PPM or less, 5 PPM or less, 4 PPM or less, 3 PPM or less, 2 PPM or less, 1 PPM or lees, or 0.5 PPM or less. In some embodiments $B_H$ is 10 parts per million (PPM) or less, 9 PPM or less, 8 PPM or less, 7 PPM or less, 6 PPM or less, 5 PPM or less, 4 PPM or less, 3 PPM or less, 2 PPM or less, 1 PPM or lees, or 0.5 PPM or less.

The examples for determining whether the coordinates of the untreated object $\vec{p}_i$ identified in step 714 and the coordinates of objects in the target object group 54 are below threshold values given above do not address the case in which the target object group 54 contains multiple objects. The target object group 54 will contain multiple objects after loop 712-722 has been repeated for multiple object sets 50 because either an untreated object or a "missing" object will be added to the target object group 54 each time loop 712-722 is repeated. There are at least two different ways that such a case can be addressed. In one approach, the coordinates of all the objects in the target object group 54 are averaged together to form an object $\vec{p}_j$ that represents the average values of all the objects in the target object group 54. The distance test is then performed between a respective object $\vec{p}_i$ in the target object set 50 and the averaged object $\vec{p}_j$. In another approach, separate distance tests given above are performed between the respective object $\vec{p}_i$ in the target object set 50 and each object in the target object group 54. In some embodiments, if any of these distance tests fail, the untreated object $\vec{p}_i$ identified in step 714 is not added to the target object group (716-No).

Step 722. In step 722, a determination is made as to whether all object sets 50 in the plurality of object sets 50 have been examined for an object that should be assigned to the target object group 54 selected in the last instance of step 710. If so (722-Yes), control passes to step 724. If not (722-No), control passes back to step 712 where another target object set 50 is selected and loop 712-722 is repeated.

Step 724. In step 724, a determination in made as to whether all object groups 54 in the plurality of object groups 54 have been examined by the above-identified process (loop 712-722). If not (724-No), process control returns to step 710 where another target object group 54 in the plurality of object groups 54 is selected and loop 712-722 is repeated for the target object group 54. If each object group 54 in the plurality of object groups 54 has been examined by an iteration of loop 712-722 (724-Yes), control passes to step 726.

Step 726. In step 726, a determination is made as to whether all objects in all objects set have been marked treated. If not (726-No), control passes to step 728, if so (726-Yes), control passes to step 730.

Step 728. In step 728, an object group 54 is added to the plurality of object groups for an untreated object in one of the object sets in the plurality of objects sets and the untreated object is placed in the newly created object group and marked treated. The newly created object group is designated as the target object group and control passes to step 712 so that the target object group can be populated with corresponding objects from object sets other than the object set that was the source of the untreated object.

Step 730. In step 730, the initial alignment proposal comprising the plurality of object groups 54 is outputted. In some embodiments, this outputting step merely means that the plurality of object groups 54 are stored, however transiently, in memory 36 and/or data storage 14, or in some other memory that is accessible by computer 10 across wide area network 34 or some other form of network. In some embodiments, this outputting step merely means that the object groups 54 are passed to an object group optimizer that performs steps such as those disclosed in FIG. 4. In some embodiments, the plurality of object groups 54 are outputted to a user interface device, a computer readable storage medium, a memory, or a local or remote computer system; or the plurality of object groups 54 are displayed.

FIGS. 3 and 7 outline two methods for the generation of an initial alignment proposal. One of skill in the art will recognize equivalent methods for generation of an initial alignment proposal and all such methods are within the scope of the disclosure. For example, referring to FIG. 7, in step 708 it is not necessary to construct a plurality of object groups at this stage in the method. Rather, once a first object set is selected, loop 712-722 can be repeated for each respective object in the first object set and the object group for a respective object in the first object set could be constructed during the first iteration of loop 712-722 for the respective object. The plurality of object groups would be constructed by repetition of loop 710-722 for each object in the first object set. Then, a new object group could be created for an object in any of the objects sets that remains marked untreated and loop 712-722 repeated for the new object group. The process of constructing a new object group for an untreated object and repeating the steps of loop 712-722 would then continue until no untreated objects remain in any of the objects set in the plurality of object sets.

Figure 4:
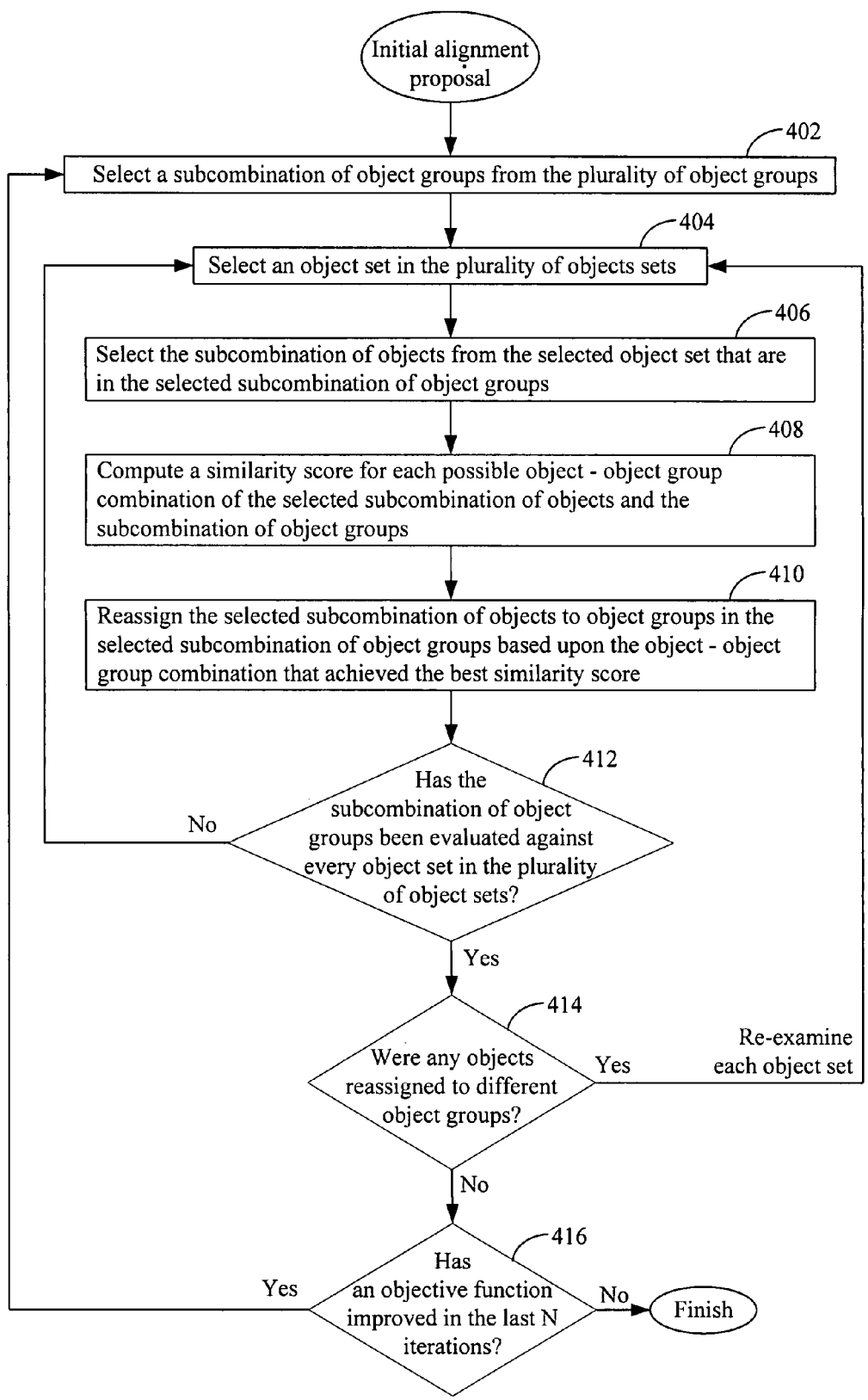
FIG. 4 illustrates a method for refining an initial alignment proposal using a greedy search algorithm in accordance with an aspect of the disclosure.

Methods for refining an initial alignment proposal are provided for situations in which the initial alignment proposal contains at least one object group in which some of the objects in the at least one object group do not correspond to each other. An exemplary approach to refining such alignment proposals is illustrated in FIG. 4. In the steps illustrated in FIG. 4, the alignment proposal is stored as a plurality of objects groups 54.

Step 402. In step 402 a subcombination of object groups 54 from the alignment proposal (the plurality of object groups) is selected. In some embodiments, three object groups from the alignment proposal are selected. In some embodiments, four object groups, five object groups, six object groups, seven object groups, eight object groups, nine object groups, or ten object groups are selected from the alignment proposal. In practice any number of object groups can be selected in step 402 up to the number of object groups 54 in the full alignment proposal (outputted in step 328) itself. Verification of the assignments of objects 200 in the selected subcombination of object groups, and possible reassignment of the objects 200 to different object groups 54 is performed by the steps in loop 404-412 as described in further detail below.

Step 404. In step 404, an object set 50 in the plurality of objects sets is selected. In typical embodiments, a given object set 50 is not selected a second time in an instance of step 404 until all of the objects sets 50 in the plurality of object sets have been selected in previous instances of step 404. For example, in some embodiments, object set 50-1 is not eligible for selection in step 404 if it has already been picked once in a previous instance of step 404 and another object set 50-N has not been picked by a previous instance of step 404. In some embodiments, an object set 50 in the plurality of object sets is picked on a random or pseudo random basis without care as to whether the same object set 50 has already been selected by an instance of step 404, provided that the selected object set differs from the object set selected in the last instance of step 404. For example, in this specific embodiment, on iteration i of step 404, object set 50-1 cannot be selected in step 404 if the object set was selected in iteration i−1 of step 404. However, object set 50-1 could be selected in iteration i+1 of step 404.

Step 406. In step 406, the subcombination of objects 200 from the object set 50 designated in step 404 that are in the subcombination of object groups defined in the last instance of step 402 are identified. For example, consider the case in which the subcombination of object groups 54 from the plurality of object groups selected in the last instance of step 402 is object groups A, B, and C. Further suppose that the object set selected in the last instance of step 404 is object set 50-1. Then, according to this example, the subcombination of objects selected from object set 50-1 in step 406 are those objects in object set 50-1 that have been assigned to object groups A, B, and C in the alignment proposal. Suppose that, as illustrated in FIG. 5, in the initial alignment proposal, object X is in object group A, object Y is in object group B, and object Z is in object group C. Of course, objects groups A, B, and C will have additional objects from the object sets of other images, but only the object set selected in the last instance of step 404 may be used to form alternative alignment proposals in step 406. Thus, as a result of step 406, N number of object groups are selected, and N objects, one for each of the N object groups is selected. It will be appreciated that FIG. 5 lists just a subcombination of object groups (groups A, B, and C) in the initial alignment proposal of step 328 and that the initial alignment proposal of step 328 typically has many more object groups (e.g., 50 or more) than just the subcombination of object groups listed in FIG. 5.

Step 408. In step 402, a subcombination of object groups 54 (e.g., object groups A, B, and C) in the plurality of object groups are selected. In step 404, an object set 50 in the plurality of objects sets is selected. In step 406, the subcombination of objects 200 from the object set selected in step 404 that are assigned to the subcombination of object groups 54 selected in step 402 (e.g., objects X, Y, and Z) are selected. In step 408, a similarity score is computed for each possible object—object group combination of the selected subcombination of objects from step 406 and the selected subcombination of object groups from step 402.

As illustrated in FIG. 5, in the case of three objects and three object groups, there are a total of six different object— object group combinations, the original proposal and five alternative alignment proposals. A similarity score is computed for each of these alternative alignment proposals. In some embodiments, a similarity score is computed as:

$$F(\text{alignment proposal}) = \sum_{\text{all object groups in the proposal}} f(\text{object group}).$$

As illustrated in FIG. 5, each object group 54 considered has multiple objects 200. In step 406, those objects 200 in a particular object set 50 are identified for permutation into all possible object—object group combinations to generate alternative alignment proposals. The objects 200 not identified in step 406 are held fixed in each of these alternative alignment proposals. For example, referring to FIG. 5, objects X, Y, and Z were selected in step 406 and so are permuted into all possible alternative alignment proposals whereas objects H, J, and K were not identified in step 406 because they are not from the object set identified in the last instance of step 404.

In some embodiments:

$$f(\text{object group}) = \sum_{\text{all pairs } \langle i,j \rangle \text{ in the group}} \text{sim}(\vec{p}_i, \vec{p}_j)$$

This objective function is essentially the total sum of similarity measures between the object pairs for all object groups. Here, $\vec{p}_i$ and $\vec{p}_j$ are the $i^{th}$ object and the $j^{th}$ object respectively, $\text{sim}(\vec{p}_i,\vec{p}_j)$ is the similarity measure between $\vec{p}_i$ and $\vec{p}_j$. For example, in such embodiments, the similarity score for the initial alignment proposal set forth in FIG. 5 is:

$$F(\text{alignment proposal}) =$$
$$f(\text{object group } A) + f(\text{object group } B) + f(\text{object group } C) =$$
$$\sum_{\text{all pairs } \langle i,j \rangle \text{ in object group } A} \text{sim}(\vec{p}_i, \vec{p}_j) +$$
$$\sum_{\text{all pairs } \langle i,j \rangle \text{ in object group } B} \text{sim}(\vec{p}_i, \vec{p}_j) +$$
$$\sum_{\text{all pairs } \langle i,j \rangle \text{ in object group } C} \text{sim}(\vec{p}_i, \vec{p}_j) =$$
$$\text{sim}(X, H) + \text{sim}(Y, J) + \text{sim}(Z, K).$$

Further, in such embodiments, the similarity score alternative alignment proposal 1 set forth in FIG. 5 is:

$$F(\text{alignment proposal}) =$$
$$f(\text{object group } A) + f(\text{object group } B) + f(\text{object group } C) =$$
$$\sum_{\text{all pairs } \langle i,j \rangle \text{ in object group } A} \text{sim}(\vec{p}_i, \vec{p}_j) +$$
$$\sum_{\text{all pairs } \langle i,j \rangle \text{ in object group } B} \text{sim}(\vec{p}_i, \vec{p}_j) +$$
$$\sum_{\text{all pairs } \langle i,j \rangle \text{ in object group } C} \text{sim}(\vec{p}_i, \vec{p}_j) =$$
$$\text{sim}(X, H) + \text{sim}(Z, J) + \text{sim}(Y, K).$$

In some embodiments, the plurality of images 46 comprise $^1H$—$^{13}C$ nuclear magnetic resonance spectra and $\text{sim}(\vec{p}_i,\vec{p}_j)$ for a given pair of objects $\vec{p}_i,\vec{p}_j$ in an object group 54 in an alignment proposal is computed using the following equation:

$$\text{sim}(\vec{p}_i,\vec{p}_j) = -\{\text{dist}(\vec{p}_i,\vec{p}_j)\}^2 = -\{(C_i-C_j)^2 + \lambda(H_i-H_j)^2\},$$
where $C_i$ is the coordinate of object $\vec{p}_i$ in the $^{13}C$ dimension;
$C_j$ is the coordinate of object $\vec{p}_j$ in the $^{13}C$ dimension;
$H_i$ is the coordinate of object $\vec{p}_i$ in the $^1H$ dimension;
$H_j$ is the coordinate of object $\vec{p}_j$ in the $^1H$ dimension; and
$\lambda$ is a normalizing constant.

In some embodiments $\lambda$ is determined by first considering the upper bounds for carbon and proton dimensions. For example, the upper bounds for carbon and proton dimensions can be estimated by manually aligning two reference object groups representing two known metabolites that are next to each other in a two-dimensional NMR spectrum. The assumption can be made that the coordinates of the carbon dimension for the object in one object group are independently drawn from a uniform distribution $[C_{true}-R_C, C_{true}+R_C]$, where $C_{true}$ is the actual coordinate in the carbon dimension for the corresponding metabolite and $R_C$ is the maximum range that an object can shift in the carbon dimension, which can be estimated in a nonbiased form from the reference data. The upper bound $B_C$ for the carbon dimension is then defined as $2R_C$. The upper bound $B_H$ for the proton dimension can be calculated in the similar way. The normalizing constant $\lambda$ is then estimated as $\{B_C/B_H\}^2$.

In some embodiments, the plurality of images 46 comprise two-dimensional spectra and $\text{sim}(\vec{p}_i,\vec{p}_j)$ for a given pair of objects $\vec{p}_i,\vec{p}_j$ in an object group 54 in an alignment proposal is computed as:

$$\text{sim}(\vec{p}_i,\vec{p}_j) = -\{\text{dist}(\vec{p}_i,\vec{p}_j)\}^2 = -\{(X_i-X_j)^2 + \lambda(Y_i-Y_j)^2\},$$
where $X_i$ is the coordinate of object $\vec{p}_i$ in the X dimension;
$X_j$ is the coordinate of object $\vec{p}_j$ in the X dimension;
$Y_i$ is the coordinate of object $\vec{p}_i$ in the Y dimension;
$Y_j$ is the coordinate of object $\vec{p}_j$ in the Y dimension; and
$\lambda$ is an optional normalizing constant.

In such embodiments $\lambda$ is determined using any suitable method for balancing the X dimension and the Y dimension. It will be appreciated that similar distance metrics can be used when the plurality of images 46 comprise three-dimensional spectra, four-dimensional spectra and higher order spectra, where additional terms are added to the distance metric (or other form of metric used to compute similarity) to handle the additional dimensions. Furthermore, other similarity metrics can be used to computer similarity in step 408, including but not limited to a Manhattan distance, a Chebychev distance, an angle between vectors, a correlation distance, a standardized Euclidean distance, a Mahalanobis distance, a squared Pearson correlation coefficient, or a Minkowski distance. Such metrics can be computed, for example, using SAS (Statistics Analysis Systems Institute, Cary, N.C.) or S-Plus (Statistical Sciences, Inc., Seattle, Wash.). Such metrics are described in Draghici, 2003, *Data Analysis Tools for DNA Microarrays*, Chapman & Hall, CRC Press London, chapter 11, which is hereby incorporated by reference herein in its entirety for such purpose.

In some embodiments, the plurality of images 46 comprises two-dimensional spectra and $\text{sim}(\vec{p}_i,\vec{p}_j)$ for a given pair of objects $\vec{p}_i,\vec{p}_j$ in an object group 54 in an alignment proposal is computed as:

$$\text{sim}(\vec{p}_i, \vec{p}_j) = \begin{cases} -\infty, \text{ if } |X_i - X_j| \text{ or } |Y_i - Y_j| \text{ is larger than an upper bound, and,} \\ -\{\text{dist}(\vec{p}_i, \vec{p}_j)\}^2, \text{ otherwise,} \end{cases}$$

where $$-\{\text{dist}(\vec{p}_i,\vec{p}_j)\}^2 = -\{(X_i - X_j)^2 + \lambda(Y_i - Y_j)^2\}; \text{ and}$$

$X_i$ is the coordinate of object $\vec{p}_i$ in the X dimension;
$X_j$ is the coordinate of object $\vec{p}_j$ in the X dimension;
$Y_i$ is the coordinate of object $\vec{p}_i$ in the Y dimension;
$Y_j$ is the coordinate of object $\vec{p}_j$ in the Y dimension; and
$\lambda$ is a normalizing constant.

In such embodiments $\lambda$ is determined using any suitable method for balancing the X dimension and the Y dimension.

In some embodiments, the plurality of images 46 comprises two-dimensional images (e.g., spectra) and $\text{sim}(\vec{p}_i,\vec{p}_j)$ for a given pair of objects $\vec{p}_i,\vec{p}_j$ in an object group 54 in an alignment proposal is computed as:

$$\text{sim}(\vec{p}_i, \vec{p}_j) = \begin{cases} -\infty, \text{ if } |X_i - Y_j| \text{ or } |X_i - Y_j| \text{ is larger than an upper bound} \\ -\{\text{dist}(\vec{p}_i, \vec{p}_j)\}^2 + \gamma \cdot \text{correlation}_{ij} - \eta \cdot (I_i - I_j)^2, \text{ otherwise,} \end{cases}$$

where $$-\{\text{dist}(\vec{p}_i,\vec{p}_j)\}^2 = -\{(X_i - X_j)^2 + \lambda(Y_i - Y_j)^2\};$$

$X_i$ is the coordinate of object $\vec{p}_i$ in the X dimension;
$X_j$ is the coordinate of object $\vec{p}_j$ in the X dimension;
$Y_i$ is the coordinate of object $\vec{p}_i$ in the Y dimension;
$Y_j$ is the coordinate of object $\vec{p}_j$ in the Y dimension;
$\lambda$ is a normalizing constant;
correlation$_{ij}$ is the correlation between a defined neighborhood of object $\vec{p}_i$ and object $\vec{p}_j$;
$\gamma$ is a weight for the correlation term correlation$_{ij}$;
$I_i$ is a log intensity of object $\vec{p}_i$;
$I_j$ is a log intensity of object $\vec{p}_j$; and
$\eta$ is a weight for $(I_i - I_j)^2$.

Such embodiments are particularly useful when replica images are available. Replica images are images taken under the exact same set of experimental conditions. In some embodiments, such replica images are averaged together to form a plurality of images that each represent two or more replica images. For example, consider the case where there are four images, A, B, C, and D, where A is a replica of B and C is a replica of D. In this case, A and B may be averaged together to form image AB and C and D may be averaged together to form image CD. Images AB and CD are then aligned using the methods described in FIGS. 3 and 4 and set forth above.

In some embodiments, a neighborhood region surrounding each object in its native image is defined. Referring to FIG. 2, these neighborhood regions are stored as one or more optional object shapes 208 for each object 200 in an object group 54.

Then, a neighborhood correlation is used to measure the shape similarity between a pair of peaks, where correlation$_{ij}$ is the correlation between the defined neighborhood of $\vec{p}_i$ and $\vec{p}_j$. In some embodiments correlation$_{ij}$ is a Pearson's correlation coefficient between the defined neighborhood of $\vec{p}_i$ and $\vec{p}_j$. The log intensity $I_i$ and $I_j$ of $\vec{p}_i$ and $\vec{p}_j$ respectively can be determined using conventional methods. Typically, in the case where an object 200 is a peak in an image 46, such methods map the area or volume encompassed by the peak.

In some embodiments, $\gamma$ is user determined to balance the position difference and the shape difference. In some embodiments, the ratio of the mean of the square distances to the mean of the correlations is used as an estimate for $\gamma$ to make the scales of the correlation term and the square distance term comparable. The two means are calculated by randomly picking a large number (e.g. 10,000) of object pairs such that any pair of objects is from different images and their position differences in both dimensions are within predetermined upper bounds. In some embodiments, $\eta$ is defined as the ratio of the standard deviation of the position shifts and the standard deviation of the log-intensity of all objects in aligned replicated images (e.g. images AB and CD in the example above), and $\eta$ is zero otherwise.

Step 410. In step 410, a selected subcombination of objects is reassigned to object groups in the selected subcombination of object groups based upon the object—object group combination alignment proposal that achieved the best similarity score. For example, referring to FIG. 5, if alignment proposal 2 achieved the best score, than object X is reassigned to object group B and object Y is reassigned to object group A. Continuing to refer to FIG. 5 if, on the other hand, the initial alignment proposal achieved the best score, than object X remains in object group A and object Y remains in object group B.

Step 412. In step 412, a determination is made as to whether the subcombination of object groups identified in the last instance of step 402 has been evaluated against every object set in the full alignment proposal (the plurality of object sets). For example, referring to FIG. 5, condition (412-Yes) will not be achieved until there has been an instance of step 404 for the object set corresponding to image 1 and another instance of step 404 for the object set corresponding to image 2. If the subcombination of object groups identified in the last instance of step 402 has not been evaluated against every object set in the full alignment proposal (412-No), control passes to step 404 where another object set in the plurality of object sets is selected. For example, referring to FIG. 5, in one iteration (instance) of step 404, the object set corresponding to image I may be selected whereas in another iteration of step 404, the object set corresponding to image 2 may be selected. When all objects sets have been selected in instances of step 404 for a given subcombination of object groups selected in step 402 (412-Yes), process control passes onto step 414.

Step 414. In step 414, a determination is made as to whether any objects were reassigned to different object groups during loop 404-414. If so (414-Yes), the objects sets are reexamined by loop 404-412. For example, referring to FIG. 5, suppose that alternative alignment proposal 1 was accepted for image 1. Then, when decision 414 is reached, the object set for image 1 and the object set for image 2 are examined again in successive instances of step 404. This pattern continues until no alternative alignment proposals are accepted for the object set for image 1 or the object set for image 2 for the given subcombination of object groups selected in step 402. When objects have not been reassigned to different object groups during an instance of loop 404-414 (414-No), process control passes to step 416.

Step 416. In step 416, a determination is made as to whether the objective function for the complete alignment proposal has improved. The objective function for the complete alignment proposal is given as $$F(\text{alignment proposal}) = \sum_{\text{all object groups in the proposal}} f(\text{object group})$$

where $$\sum_{\text{all object groups in the proposal}} f(\text{object group})$$

is computed using any of the methods set forth above. If the objective function has improved in the last N iterations of loop 402-416, where N is 1, 2, 3, 4, 5, 6 or greater in various embodiments, (416-Yes), than process control returns to step 402 where a new subcombination of object groups form the plurality of object groups is selected. If the objective function has not improved in the last N iterations of loop 402-416 (416-No), than the object groups in their final form are outputted as the final alignment proposal. In some embodiments, the output of the final output proposal means that the object groups 54 containing the final alignment proposal are stored, however transiently, in memory 36 and/or data storage 14, or in some other memory that is accessible by computer 10 across wide area network 34. In some embodiments, the plurality of object groups containing the final output proposal are outputted to a user interface device, a computer readable storage medium, a memory, or a local or remote computer system; or the plurality of object groups are displayed.

The process outlined in FIG. 4 is an example of a greedy search algorithm. In alternative embodiments variations of the search algorithm are taken. For instance, in some embodiments, step 416 continues to loop back to step 402 until each possible subcombination of N object groups from the plurality of object groups M in the full alignment proposal have been selected, where N is held constant (e.g., N=3) and N<M. So for example, in some embodiments, there may be 10 object groups 54 in the full alignment proposal and step 416 loops back to step 402 until each subcombination of 3 object groups 54 in the full set of 10 object groups 54 has been selected. In some embodiments, the number of object groups in the subcombination of object groups selected in each iteration of step 402 is a fixed number, such as 3 object groups 54. In other embodiments, the number of object groups in the subcombination of object groups selected in each iteration of step 402 is allowed to vary. For example, in some embodiments, in one iteration of step 402, five object groups 54 are selected whereas in another iteration of step 402, four object groups 54 are selected. In still other embodiments, the condition 416-No is achieved regardless of whether the objective function is still improving after a fixed number of iterations of loop 402-416. For example, in some embodiments, the condition 416-No is achieved regardless of whether the objective function is still improving after loop 402-416 has been repeated more than twice, more than ten times, more than 100 times, more than 1000 times, more than one hundred thousand times, or more than a million times. Any of these alternative search embodiments are forms of greedy search algorithms.

In fact, any greedy search algorithm, that is, any algorithm that follows the problem solving metaheuristic of making the locally optimum choice at each stage with the hope of finding the global optimum, can be used to refine the initial alignment proposal 328. The algorithm disclosed in FIG. 4 merely serves to provide an example of one such algorithm. Additional disclosure on greedy algorithms is found in Cormen et al., 1990, *Introduction to Algorithms* Chapter 17 "Greedy Algorithms" p. 329; Cormen, 2001, *Introduction to Algorithms*, Chapter 16; Gutin et al., 2002, Discrete Applied Mathematics 117, 81-86; Bang-Jensen et al., 2004, Discrete Optimization 1, 121-127; and Bendall and Margot, 2006, Discrete Optimization 3, 288-298, each of which is incorporated by reference herein for their teaching of greedy algorithms.

In some embodiments, a dynamic search rather than a greedy search algorithm is used to refine the initial alignment proposal 328 rather than the process illustrated in FIG. 4. In some embodiments, a hybrid between a dynamic search and a greedy search algorithm is used to refine the initial alignment proposal 328 rather than the process illustrated in FIG. 4. Exemplary dynamic approaches that can be used are disclosed in Cormen et al., 2001, *Introduction to Algorithms*, $2^{nd}$ ed. MIT Press & McGraw-Hill, chpt. 15: 323-69; Stokey et al., 1989, *Recursive Methods in Economic Dynamics*, Harvard Univ. Press; Bertsekas, 2000, *Dynamic Programming and Optimal Control*, $2^{nd}$ ed. Athena Scientific, Vols. 1 and 2; and Giegerich et al., 2004, Science of Computer Programming, Vol 51, 3:215-263, each of which is hereby incorporated by reference herein in its entirety for disclosure of dynamic searches. Dynamic programming (a dynamic search) makes use of (i) overlapping subproblems, (ii) optimal substructure, and (iii) memorization. Dynamic programming usually takes one of two approaches: the top-down approach, or the bottom-up approach. In the top-down approach, the problem is broken into subproblems, and these subproblems are solved and the solutions remembered, in case they need to be solved again. This is recursion and memorization combined together. In the bottom-up approach, all subproblems that might be needed are solved in advance and then used to build up solutions to larger problems.

Some embodiments take advantage of the fact that, typically, each experimental condition involves multiple replicates. In such embodiments, the strategy is to first align objects in the replicates for each condition. This can be done using the methods illustrated in FIGS. 3 and 4 and described above, where each image is a replicate taken under the same experimental conditions. Then, an average image is created for each condition. Lastly, these averaged images are aligned across all experimental conditions using the methods illustrated in FIGS. 3 and 4 and described above, where each image is an averaged image from multiple replicates. In some embodiments, for the objects representing the same observable (e.g., metabolite) in the replicates, signal intensity is also considered tracked and used to align objects in the manner described above. In some embodiments, each experimental condition is a different perturbation, or absence of such a perturbation to which a sample is exposed or not exposed prior to measurement of the sample.

EXAMPLES

Differential inbred strain susceptibility to acetaminophen-induced hepatotoxicity.

For the genetic analysis, the susceptibility of a panel of 16 inbred mouse strains to developing liver toxicity after a single 300 mg/kg intraperitoneal dose of acetaminophen was assessed. This dose is known to cause liver toxicity in mice. During the 24 hour period after dosing, serum alanine aminotransferase (ALT), morbidity and liver histochemistry were assessed as indices of liver toxicity. There was variability in the severity of the toxicity observed in different experiments. However, 15 strains reproducibly developed liver toxicity after receiving this dose of acetaminophen. In addition to the increase in serum ALT, acetaminophen exposure caused mortality in a significant percent of the mice from these 15 strains. However, the SJL strain was reproducibly resistant to developing drug-induced liver toxicity. There was no mortality among SJL mice after acetaminophen exposure; and they had a much smaller and transient increase in serum ALT.

To uncover the genetic basis for these inter-strain differences, a detailed histochemical, transcriptional, and metabolomic analysis of the drug-induced response in livers obtained from resistant (SJL) and three selected sensitive (C57BL6, DBA/2, and SMJ) strains was performed. Within forty-eight hours after acetaminophen treatment, there was at least 60% mortality among mice from the three sensitive strains, whereas all SJL mice survived. In addition, the three sensitive strains had a distinct pattern of morbidity. C57B6 mice had 100% mortality within six hours after dosing, while mortality in the SMJ and DBA/2 strains occurred at 24 and 48 hours after dosing, respectively. Histological examination of liver tissue sections confirmed the biochemical and morbidity analyses. Liver tissue from SJL mice had relatively minor drug-induced injury. However, liver tissue obtained from the three sensitive strains showed quite extensive centrilobular necrosis.

Differential susceptibility to a hepatotoxic dose of acetaminophen could result from differences in the rate of production of the reactive quinone metabolite that causes liver toxicity. However, the resistant SJL strain has previously been shown to generate the same amount of hepatic acetaminophen-protein adducts after acetaminophen treatment as the sensitive C57B6 strain. In addition, the hepatic gene expression profiles indicated that acetaminophen treatment induced an equivalent (or greater) level of DNA damage in SJL mice relative to that in the three sensitive strains. The level of expression of three different genes that are indicators of the DNA damage response (Ddit3, Dnajb1, and Gadd45ga) was increased to the same extent in all four strains. Thus, a hepatotoxic dose of acetaminophen induces the formation of protein adducts and activates the DNA damage response in resistant SJL mice to the same extent as in the susceptible strains. This suggests that genetic differences affecting the host response to the toxic metabolites underlie the strain-specific differences in susceptibility to acetaminophen-induced liver toxicity. Furthermore, the fact that only a single strain was resistant and the variability in the response among the sensitive strains suggests that more than one genetic factor is likely to contribute to resistance among the inbred strains.

Analysis of acetaminophen-induced endogenous metabolite and gene expression changes. Endogenous metabolites and gene expression changes in liver were examined at 0, 3 and 6 hours after acetaminophen exposure in the resistant (SJL) and three sensitive strains (DBA, SMJ and C57) strains in order to identify the pathways and genes contributing to resistance to acetaminophen-induced liver toxicity. The endogenous metabolites were profiled using $^1H-^{13}C$ two-dimensional-NMR analysis. Over 400 metabolite peaks were quantified and analyzed by this method, and principal component analysis (PCA) (Duda, 2001, *Pattern Classification*, John Wiley & Sons, Inc., pp. 568-569, which is hereby incorporated by reference herein) was used to identify metabolite peaks that distinguished the response of the sensitive strain from the three resistant strains. The metabolite profiles obtained three hours after drug treatment differentiated resistant SJL mice from the three sensitive strains.

Therefore, the metabolites within the peaks that distinguished the response of the resistant strain from the three sensitive strains at zero and three hours after drug exposure were identified. Nine endogenous metabolite peaks had a unique abundance pattern in the resistant SJL strain, which were qualitatively and quantitatively distinct from those in the three sensitive strains. Using resonance assignments and confirmation experiments with purified compounds, the identity of eight of these nine peaks was determined. Three peaks were assigned to glutathione. Consistent with its resistance to acetaminophen-induced liver toxicity, SJL was the only strain that maintained its hepatic glutathione concentration three hours after acetaminophen administration; hepatic glutathione levels were significantly decreased in the three sensitive strains. Five other metabolite peaks were assigned to alanine, lactate and betaine. Microarrays were simultaneously used to analyze gene expression in liver obtained from these four strains before (zero hr) and three hours after acetaminophen administration. Using pre-determined selection criteria (fold-change>2 and p-value<0.01), the resistant SJL strain had 224 genes with an expression pattern that significantly differed from that in the three sensitive strains three hours after treatment. This large number of differentially expressed genes limited the utility of analyzing the gene expression data by itself. However, an integrated analysis of the gene expression and metabolite data provided a more restricted set of pathways and genes to consider. Only twenty of these differentially expressed genes were functionally annotated in the Gene Ontology database as being involved in metabolism. Moreover, only three genes (Pdk4, G6pc, and Bhmt2) were in pathways related to the four endogenous metabolites identified by the metabolomic data.

Animal husbandry and drug treatment. Seven to eight week old male mice were obtained from Jackson Laboratory (Bar Harbor, Me.) and acclimatized for an additional week before use. The following 16 inbred mouse strains were studied: SJL, LGJ, BALB/cJ, DBA/2J, A/J, AKR/J, A/HeJ, 129/SvJ, B10.D2-H2/oSNJ, C57BL/6J, NZW/LaCJ, NZB/BInJ, MRL/MpJ, C3H/HeJ, LP/J, SM/J. The mice were housed under pathogen-free environment and provided food and water ad libitum with a 12h: 12h light: dark cycle until experimental use. Before each experiment, food was withheld from the animals overnight (greater than sixteen hours) to uniformly deplete hepatic glutathione stores. All mice were administered a single 300 mg/kg intraperitoneal dose of freshly prepared acetaminophen (Voigt Global Distribution Inc.) suspended in PBS (pH 7.4), and were allowed free access to food and water after treatment. The mice were euthanized by $CO_2$ inhalation to collect blood samples and liver tissues at zero, three, and six hours after dosing. The remaining mice were monitored for 48 hours for the occurrence of acetaminophen-induced deaths. Blood samples were withdrawn by cardiac puncture and placed in EDTA-coated tubes, and plasma samples were isolated by centrifugation. Alanine aminotransferase (ALT) activity was measured at the Marshfield Clinic Laboratories (Marshfield, Wis.). Liver tissues were removed immediately and cut into two sections. The smaller section was fixed in buffered formalin, processed by standard histological techniques, stained with hematoxylin and eosin, and examined for histopathologic evidence of liver injury. The remaining sections were snap-frozen in liquid nitrogen and stored at −80° C. for gene expression and metabolite analysis.

Metabolite extraction, NMR analysis, and data processing. Frozen liver tissues (~500 mg) were pulverized with liquid nitrogen and immediately plunged into 15 ml of a cold solution of 67% MeOH/33% water. Tissues were lysed by freezing and thawing three times, thoroughly mixed, and then centrifuged at 12,000×g for 30 minutes at 4° C. The supernatants were dried by speed-vacuum and re-suspended in 500 µl $D_2O$ (Cambridge Isotope Laboratories, Inc.). Samples were then centrifugally filtered through 10-kDa cutoff filters (Microcon YM-10, Millipore) to remove precipitated proteins. The filtrate was lyophilized and dissolved in 200 µl $D_2O$ containing 1 mM sodium-3-(tri-methylsilyl)-2,2,3,3-tetra-deuteriopropionate (TSP; Sigma-Aldrich), which was an internal standard for NMR analysis.

NMR spectra were recorded at 300°K on a Bruker Avance 600 MHz spectrometer operating at $^1H$ frequency of 599.99 MHz and $^{13}C$ frequency of 150.87 MHz using a 3 mm Nalorac microprobe with z-axis pulsed-field gradient. Resonances were assigned using 1D proton spectra, 2D proton correlated spectroscopy COSY, and 2D $^1H$—$^{13}C$ single-bond correlated HSQC spectra. Peaks used in the quantitative metabolite analyses were picked from 2D $^1H$—$^{13}C$ HSQC spectra acquired using z-axis pulsed field gradients for coherence selection. Spectra were acquired using 16 to 64 scans per FID, 1024 and 256 points for the $^1H$ and $^{13}C$ dimensions, and total spectrum acquisition times of 2.75 to 11 hours. NMR assignments were confirmed by acquiring the spectra of samples spiked with purified compounds.

2D-NMR spectra were processed with Topspin (Bruker, Billerica, Mass.) and interpreted with the aid of the Sparky Assignment and Integration Software package (UCSF, San Francisco Calif.). The algorithm described above in conjunction with FIGS. 1 through 5, was used to align the peaks occurring in different spectra that corresponded to the same metabolite. In brief, the alignment was performed in two steps. In the first step, replicates for the same strain were aligned and the averages of the aligned clusters were used to generate a representative spectrum for that strain. The representative spectra were then aligned to create the final alignment of the NMR data. The aligned peak clusters were then filtered using the following criteria: (1) the metabolite peak was present in more than four samples obtained from the different strains and time-points; (2) the maximal intensity of the peak was larger than ten; (3) the fold-change of the maximal to the minimal intensity was greater than five; (4) the peaks with a spectral region ($^{13}C$: 61-81; $^1H$: 3.3-4.3) were excluded because they were highly overlapping. Peaks meeting these criteria were then ranked by their ANOVA p-values.

Alternative Embodiments and References Cited

All references cited herein are incorporated by reference herein in their entirety and for all purposes to the same extent as if each individual publication or patent or patent application was specifically and individually indicated to be incorporated by reference in its entirety for all purposes.

Each of the methods, computer program products, and computers disclosed herein optionally further comprise a step of, or instructions for, outputting a result (for example, to a monitor, to a user, to computer readable media, e.g., storage media or to a remote computer).

The present invention can be implemented as a computer program product that comprises a computer program mechanism embedded in a computer readable storage medium. Further, any of the methods of the present invention can be implemented in one or more computers or computer systems. Further still, any of the methods of the present invention can be implemented in one or more computer program products. Some embodiments of the present invention provide a computer system or a computer program product that encodes or has instructions for performing any or all of the methods disclosed herein. Such methods/instructions can be stored on a CD-ROM, DVD, magnetic disk storage product, or any other computer readable data or program storage product. Such methods can also be embedded in permanent storage, such as ROM, one or more programmable chips, or one or more application specific integrated circuits (ASICs). Such permanent storage can be localized in a server, 802.11 access point, 802.11 wireless bridge/station, mobile electronic device, or other electronic devices. Such methods encoded in the computer program product can also be distributed electronically, via the Internet or otherwise, by transmission of a computer data signal (in which the software modules are embedded) either digitally or on a carrier wave.

What is claimed:

1. A method for aligning objects in a plurality of object sets, each object set in the plurality of objects sets comprising a plurality of objects in a corresponding image in a plurality of images, wherein each of the objects in each of the plurality of objects sets are initially marked as untreated, the method comprising:
    (A) constructing, for each respective object in a first object set in the plurality of object sets, a corresponding object group that contains the respective object in the first object set, thereby constructing a plurality of object groups;
    (B) computing, for each respective untreated object in a target object set in the plurality of object sets, a similarity metric between a target object group in the plurality of object groups and the respective object, thereby computing a plurality of similarity metrics, wherein
        the object in the target object set that has the best similarity score to the target object group is added to the target object group and marked as treated when the coordinate differences between the object and the target object group are below threshold values; and, otherwise,
        adding a missing object to the target object group when the coordinate differences between the object and the target object group are not below threshold values;
    (C) repeating the computing step (B) for each remaining object set in the plurality of object sets thereby populating the target object group; and
    (D) repeating the computing step (B) for each remaining respective object group in the plurality of objects groups, where the respective object group is designated as the target object group, wherein objects that are in the same object group are deemed to correspond to each other, thereby aligning objects in the plurality of object sets.

2. The method of claim 1, wherein each object in the plurality of objects of an object set in the plurality of object sets is characterized by a first dimension value X and a second dimension value Y.

3. The method of claim 2, wherein the first dimension value X is for carbon (C) and the second dimension value Y is for hydrogen (H), and wherein the coordinate differences between the object in the target object set that has the best similarity score to the target object group and the target object group in step (B) is below threshold values when $$|C^2-C^1|<B_C, \text{ and}$$

$$|H^2-H^1|<B_H$$

where
    $C^2$ is the first dimension indicator for the object in the target object set that has the best similarity score to the target object group;

$C^1$ is the first dimension indicator for the target object group;
$H^2$ is the second dimension indicator for the object in the target object set that has the best similarity score to the target object group;
$H^1$ is the second dimension indicator for the target object group;
$B_C$ is the first dimension threshold limit; and
$B_H$ is the second dimension threshold limit.

4. The method of claim 1, wherein each image in the plurality of images is a two-dimensional image.

5. The method of claim 1, wherein each image in the plurality of images is an N-dimensional image, wherein N is equal to 1 or greater.

6. The method of claim 5, wherein a coordinate difference between the object in the target object set that has the best similarity score to the target object group and the target object group in step (B) is below threshold values when $$|C_1^2 - C_1^1| < B_1,$$

$$|C_2^2 - C_2^1| < B_2$$

$$\ldots$$

$$|C_N^2 - C_N^1| < B_N$$

where
$C_i^2$ is the $i^{th}$ dimension indicator for the object in the target object set that has the best similarity score to the target object group;
$C_i^1$ is the $i^{th}$ dimension indicator for the target object group; and
$B_i$ is the $i^{th}$ dimension threshold limit.

7. The method of claim 1, wherein each image in the plurality of images is a two-dimensional image.

8. The method of claim 1, wherein an image in the plurality of images is a two-dimensional $^1H$—$^{13}C$ nuclear magnetic resonance spectrum and the objects in the image are peaks in the two-dimensional $^1H$—$^{13}C$ nuclear magnetic resonance spectrum.

9. The method of claim 1, wherein an image in the plurality of images is a two-dimensional nuclear magnetic resonance (NMR) spectrum, a three-dimensional NMR spectrum, or a four-dimensional NMR spectrum and the objects in the image are peaks in the two-dimensional, three-dimensional, or four-dimensional NMR spectrum.

10. The method of claim 1, wherein an image in the plurality of images is a 2D nuclear Overhauser enhancement and exchange (NOESY) spectrum, a two-dimensional J-resolved (2D-J) spectrum, a homonuclear 2D correlated (COSY) spectrum, a 2D spin-echo correlated (SECSY) spectrum, a relayed coherence-transfer (RELAYED-COSY) spectrum, a $^1H$—$^{15}N$ COSY spectrum, a $^1H$—$^{31}P$ COSY spectrum, a $^{113}Cd$—$^1H$ COSY spectrum, a rotating-frame NOE (ROESY) spectrum, a total correlation (TOCSY) spectrum, a heteronuclear single quantum correlation (HSQC) spectrum, a heteronuclear multiple-quantum coherence (HMQC) spectrum, a heteronuclear multiple bond correlation (HMBC) spectrum, a two-dimensional heteronuclear correlation (HETCOR) spectrum, a double quantum filtered correlation (DQFC) spectrum, or a two-dimensional INADAQUATE spectrum.

11. The method of claim 1, wherein an image in the plurality of images is a two-dimensional heteronuclear magnetic resonance spectrum and objects in the image are peaks in the two-dimensional heteronuclear magnetic resonance spectrum.

12. The method of claim 1, wherein an image in the plurality of images is a two-dimensional homonuclear magnetic resonance spectrum and objects in the image are peaks in the two-dimensional homonuclear magnetic resonance spectrum.

13. The method of claim 1, wherein an object set in the plurality of object sets comprises 50 objects.

14. The method of claim 1, wherein an object set in the plurality of object sets comprises 200 objects.

15. The method of claim 1, wherein the plurality of images comprise $^1H$—$^{13}C$ nuclear magnetic resonance spectra and wherein a similarity metric computed in step (B) between the object $\vec{p}_i$ having the best similarity score to the target object group $P = \{\vec{p}_1, \ldots, \vec{p}_J\}$ is computed according to the formula:

$$\text{sim}(\vec{p}_i, P) = -\sum_{j=1}^{J} \{\text{dist}(\vec{p}_i, \vec{p}_j)\}^2 = -\sum_{j=1}^{J} \{(C_i - C_j)^2 + \lambda(H_i - H_j)^2\}$$

where
$C_i$ is the coordinate of $\vec{p}_i$ in the $^{13}C$ dimension;
$C_j$ is the coordinate of $\vec{p}_j$ in the $^{13}C$ dimension;
$H_i$ is the coordinate of $\vec{p}_i$ in the $^1H$ dimension;
$H_j$ is the coordinate of $\vec{p}_j$ in the $^1H$ dimension; and
$\lambda$ is a normalizing constant.

16. The method of claim 1, wherein the similarity metric between the object and the target object group has the best similarity score when a similarity metric between the object and the target object group is greater than the similarity metric between any other object in the target object set and the target object group.

17. The method of claim 1, wherein the similarity metric between the object and the target object group has the best similarity score when a similarity metric between the object and the target object set is less than the similarity metric between any other object in the target object set and the target object group.

18. The method of claim 1, the method further comprising optimizing the assignment of objects in the plurality of object groups.

19. The method of claim 18, wherein the optimizing step comprises:
(i) selecting a subcombination of object groups in the plurality of object groups;
(ii) selecting the subcombination of objects from an object set in the plurality of objects sets that are assigned to the subcombination of object groups;
(iii) computing a similarity score for each possible object—object group combination of the selected subcombination of objects and the selected subcombination of object groups; and
(iv) reassigning the selected subcombination of objects in the object set to object groups in the selected subcombination of object groups based upon the object—object group combination that achieved the best similarity score in step (iii).

20. The method of claim 19, wherein steps (ii), (iii) and (iv) are repeated for each object set in the plurality of object sets.

21. The method of claim 19, wherein steps (i), (ii), (iii), and (iv) are repeated for a different subcombination of object groups in the plurality of object groups.

22. The method of claim 21, wherein steps (ii), (iii), and (iv) are repeated for each object set in the plurality of object sets with the given different subcombination of object groups in the plurality of object groups.

23. The method of claim 19, wherein steps (i), (ii), (iii), and (iv) are repeated several times, and wherein each repetition of steps (i), (ii), (iii), and (iv) is for a different subcombination of object groups in the plurality of object groups.

24. The method of claim 23, wherein, for each different subcombination of object groups in the plurality of object groups, steps (ii), (iii) and (iv) are repeated for each object set in the plurality of objects sets.

25. The method of claim 19, the method further comprising:
(v) repeating steps (ii), (iii) and (iv) for each object set in the plurality of object sets;
(vi) determining whether a value for an objective function has improved relative to a value for the objective function before step (v); and
repeating steps (i), (ii), (iii), and (iv) for a different subcombination of object groups in the plurality of object groups when the objective function has improved; and
terminating the optimizing step (E), when the objective function has not improved.

26. The method of claim 25, wherein the objective function, denoted F (alignment proposal), is:

$$F(\text{alignment proposal}) = \sum_{k=1, \text{all object groups in the plurality of object groups}} f(\text{object group}_k)$$

where $$f(\text{object group}_k) = \sum_{\text{all pairs } <i,j> \text{ in object group } k} \text{sim}(\vec{p}_i, \vec{p}_j).$$

27. The method of claim 26, wherein the plurality of images comprises a $^1$H—$^{13}$C nuclear magnetic resonance spectrum and wherein $$\text{sim}(\vec{p}_i,\vec{p}_j) = -\{\text{dist}(\vec{p}_i,\vec{p}_j)\}^2 = -\{(C_i-C_j)^2 + \lambda(H_i-H_j)^2\},$$
wherein $C_i$ is the coordinate of object $\vec{p}_i$ in object group k in the $^{13}$C dimension;
$C_j$ is the coordinate of object $\vec{p}_j$ in object group k in the $^{13}$C dimension;
$H_i$ is the coordinate of object $\vec{p}_i$ in object group k in the $^1$H dimension;
$H_j$ is the coordinate of object $\vec{p}_j$ in object group k in the $^1$H dimension; and
$\lambda$ is a normalizing constant.

28. The method of claim 26, wherein the plurality of images comprises a two-dimensional spectrum and wherein $$\text{sim}(\vec{p}_i,\vec{p}_j) = -\{\text{dist}(\vec{p}_i,\vec{p}_j)\}^2 = -\{(X_i-X_j)^2 + \lambda(Y_i-Y_j)^2\},$$
wherein $X_i$ is the coordinate of object $\vec{p}_i$ in object group k in the X dimension;
$X_j$ is the coordinate of object $\vec{p}_j$ in object group k in the X dimension;
$Y_i$ is the coordinate of object $\vec{p}_i$ in object group k in the Y dimension;
$Y_j$ is the coordinate of object $\vec{p}_j$ in object group k in the Y dimension; and
$\lambda$ is a normalizing constant.

29. The method of claim 26, wherein the plurality of images comprises a two-dimensional spectrum and wherein $$\text{sim}(\vec{p}_i, \vec{p}_j) = \begin{cases} -\infty, \text{ if } |X_i - X_j| \text{ or } |Y_i - Y_j| \text{ is larger than an upper bound, and} \\ -\{\text{dist}(\vec{p}_i, \vec{p}_j)\}^2, \text{ otherwise,} \end{cases}$$

wherein $-\{\text{dist}(\vec{p}_i,\vec{p}_j)\}^2 = -\{(X_i-X_j)^2 + \lambda(Y_i-Y_j)^2\};$ $X_i$ is the coordinate of object $\vec{p}_i$ in object group k in the X dimension;
$X_j$ is the coordinate of object $\vec{p}_j$ in object group k in the X dimension;
$Y_i$ is the coordinate of object $\vec{p}_i$ in object group k in the Y dimension;
$Y_j$ is the coordinate of object $\vec{p}_j$ in object group k in the Y dimension; and
$\lambda$ is a normalizing constant.

30. The method of claim 26, wherein the plurality of images comprises a two-dimensional spectrum and wherein $$\text{sim}(\vec{p}_i, \vec{p}_j) = \begin{cases} -\infty, \text{ if } |X_i - Y_j| \text{ or } |X_i - Y_j| \text{ is larger than an upper bound, and} \\ -\{\text{dist}(\vec{p}_i, \vec{p}_j)\}^2 + \gamma \cdot \text{correlation}_{ij} - \eta \cdot (I_i - I_j)^2, \text{ otherwise,} \end{cases}$$

wherein $-\{\text{dist}(\vec{p}_i,\vec{p}_j)\}^2 = -\{(X_i-X_j)^2 + \lambda(Y_i-Y_j)^2\};$ $X_i$ is the coordinate of object $\vec{p}_i$ in object group k in the X dimension;
$X_j$ is the coordinate of object $\vec{p}_j$ in object group k in the X dimension;
$Y_i$ is the coordinate of object $\vec{p}_i$ in object group k in the Y dimension;
$Y_j$ is the coordinate of object $\vec{p}_j$ in object group k in the Y dimension;
$\lambda$ is a normalizing constant;
correlation$_{ij}$ is the correlation between a defined neighborhood of object $\vec{p}_i$ and object $\vec{p}_j$;
$\gamma$ is a weight for the correlation term correlation$_{ij}$;
$I_i$ is a log intensity of object $\vec{p}_i$;
$I_j$ is a log intensity of object $\vec{p}_j$; and
$\eta$ is a weight for $(I_i-I_j)^2$.

31. The method of claim 18, wherein the optimization of the assignment of objects in the plurality of object groups is performed using a greedy search algorithm, a dynamic search, or a combination of a greedy search and a dynamic search.

32. The method of claim 1, wherein an object in an object set in the plurality of object sets corresponds to a metabolite.

33. The method of claim 1, wherein the plurality of images are replicate spectra taken under a first experimental condition, the method further comprising using the plurality of object groups to combine the plurality of images into a single first average spectrum.

34. The method of claim 33, wherein steps (A) through (C) are repeated for a different second plurality of images, wherein the different second plurality of images are replicate spectra taken under a second experimental condition, the method further comprising using the plurality of object groups to combine the different second plurality of images into a single second average spectrum.

35. The method of claim 34, wherein steps (A) through (C) are repeated to align the first average spectrum and the second average spectrum.

36. The method of claim 1, the method further comprising outputting the plurality of object groups to a user interface device, a computer readable storage medium, a memory, or a local or remote computer system; or displaying the plurality of object groups.

37. The method of claim 1, the method further comprising aligning the plurality of images based upon object assignments within the plurality of the plurality of object groups.

38. The method of claim 37, the method further comprising outputting the plurality of aligned images to a user interface device, a computer readable storage medium, a memory, or a local or remote computer system; or displaying the plurality of aligned images.

39. An apparatus for aligning objects in a plurality of object sets, each object set in the plurality of objects sets comprising the objects in a corresponding image in a plurality of images, the apparatus comprising:
   a central processing unit; and
   a memory, coupled to the central processing unit, the memory comprising:
      instructions for accessing said plurality of object sets;
      an image comparison module, the image comparison module comprising instructions for:
      (A) constructing, for each respective object in a first object set in the plurality of object sets, a corresponding object group that contains the respective object in the first object set, thereby constructing a plurality of object groups;
      (B) computing, for each respective untreated object in a target object set in the plurality of object sets, a similarity metric between a target object group in the plurality of object groups and the respective object, thereby computing a plurality of similarity metrics, wherein
      the object in the target object set that has the best similarity score to the target object group is added to the target object group and marked as treated when the coordinate differences between the object and the target object group are below threshold values; and, otherwise,
      adding a missing object to the target object group when the coordinate differences between the object and the target object group are not below threshold values;
      (C) repeating the computing step (B) for each remaining object set in the plurality of object sets thereby populating the target object group; and
      (D) repeating the computing step (B) for each remaining respective object group in the plurality of objects groups, where the respective object group is designated as the target object group, wherein objects that are in the same object group are deemed to correspond to each other, thereby aligning objects in the plurality of object sets.

40. The apparatus of claim 39, wherein the comparison module further comprises instructions for:
   (E) outputting the plurality of object groups to a user interface device, a computer readable storage medium, a memory, or a local or remote computer system; or displaying the plurality of object groups.

41. An apparatus for aligning objects in a plurality of object sets, each object set in the plurality of objects sets comprising the objects in a corresponding image in a plurality of images, the apparatus comprising:
   a central processing unit; and
   a memory, coupled to the central processing unit, the memory comprising:
      (A) means for accessing said plurality of object sets;
      (B) means for constructing, for each respective object in a first object set in the plurality of object sets, a corresponding object group that contains the respective object in the first object set, thereby constructing a plurality of object groups;
      (C) means for computing, for each respective untreated object in a target object set in the plurality of object sets, a similarity metric between a target object group in the plurality of object groups and the respective object, thereby computing a plurality of similarity metrics, wherein
      the object in the target object set that has the best similarity score to the target object group is added to the target object group and marked as treated when the coordinate differences between the object and the target object group are below threshold values; and, otherwise,
      adding a missing object to the target object group when the coordinate differences between the object and the target object group are not below threshold values;
      (D) means for repeating the means for computing (C) for each remaining object set in the plurality of object sets thereby populating the target object group; and
      (E) means for repeating the means for computing (C) for each remaining respective object group in the plurality of objects groups, where the respective object group is designated as the target object group, wherein objects that are in the same object group are deemed to correspond to each other, thereby aligning objects in the plurality of object sets.

42. The apparatus of claim 41, wherein the memory further comprises:
   (F) means for outputting the plurality of object groups to a user interface device, a computer readable storage medium, a memory, or a local or remote computer system; or displaying the plurality of object groups.

43. An apparatus for aligning objects in a plurality of object sets stored on a non-transitory computer readable storage media, the storage media comprising:
   (A) a first plurality of binary values for accessing said plurality of object sets;
   (B) a second plurality of binary values for constructing, for each respective object in a first object set in the plurality of object sets, a corresponding object group that contains the respective object in the first object set, thereby constructing a plurality of object groups;
   (C) a third plurality of binary values for computing, for each respective untreated object in a target object set in the plurality of object sets, a similarity metric between a target object group in the plurality of object groups and the respective object, thereby computing a plurality of similarity metrics, wherein
   the object in the target object set that has the best similarity score to the target object group is added to the target object group and marked as treated when the coordinate differences between the object and the target object group are below threshold values; and, otherwise,
   adding a missing object to the target object group when the coordinate differences between the object and the target object group are not below threshold values;

(D) a fourth plurality of binary values for repeating the computing (C) for each remaining object set in the plurality of object sets thereby populating the target object group; and (E) a fifth plurality of binary values for repeating the computing (C) for each remaining respective object group in the plurality of objects groups, where the respective object group is designated as the target object group, wherein objects that are in the same object group are deemed to correspond to each other, thereby aligning objects in the plurality of object sets.

44. The apparatus of claim 43, wherein the storage media further comprises:

(F) a sixth plurality of binary values for outputting the plurality of object groups to a user interface device, a computer readable storage medium, a memory, or a local or remote computer system; or displaying the plurality of object groups.

45. A method for aligning objects in a plurality of object sets, each object set in the plurality of objects sets comprising the objects in a corresponding image in a plurality of images, the method comprising:

(A) constructing, for each respective object in a first object set in the plurality of object sets, a corresponding object group that contains the respective object in the first object set, thereby constructing a plurality of object groups;

(B) computing, for each respective object in an object set in the plurality of object sets, a similarity metric between (i) the respective object and (ii) objects in an object group in the plurality of object groups thereby computing a plurality of similarity metrics, wherein the respective object is added to a first object group in the plurality of object groups when the similarity metric between the respective object and objects in the first object group is better than the similarity metric between the respective object and objects in any other object group in the plurality of object groups and (ii) coordinate differences between the respective object and objects in the first object group are below threshold values; and otherwise, adding to the plurality of object groups a new object group that comprises the respective object; and (C) repeating the computing step (B) for each remaining object set in the plurality of object sets, wherein objects that are in the same object group are deemed to correspond to each other, thereby aligning objects in the plurality of object sets.

46. The method of claim 45, the method further comprising optimizing the assignment of objects in the plurality of object groups.

47. The method of claim 46, wherein the optimizing step comprises:

(i) selecting a subcombination of object groups in the plurality of object groups;

(ii) selecting the subcombination of objects from an object set in the plurality of objects sets that are assigned to the subcombination of object groups;

(iii) computing a similarity score for each possible object—object group combination of the selected subcombination of objects and the selected subcombination of object groups; and (iv) reassigning the selected subcombintation of objects in the object set to object groups in the selected subcombination of object groups based upon the object—object group combination that achieved the best similarity score in step (iii).

48. The method of claim 47, wherein steps (ii), (iii) and (iv) are repeated for each object set in the plurality of object sets.

49. The method of claim 47, wherein steps (i), (ii), (iii), and (iv) are repeated for a different subcombination of object groups in the plurality of object groups.

50. The method of claim 49, wherein steps (ii), (iii), and (iv) are repeated for each object set in the plurality of object sets with the given different subcombination of object groups in the plurality of object groups.

51. The method of claim 47, wherein steps (i), (ii), (iii), and (iv) are repeated several times, and wherein each repetition of steps (i), (ii), (iii), and (iv) is for a different subcombination of object groups in the plurality of object groups.

52. The method of claim 51, wherein, for each different subcombination of object groups in the plurality of object groups, steps (ii), (iii) and (iv) are repeated for each object set in the plurality of objects sets.

53. The method of claim 47, the method further comprising:

(v) repeating steps (ii), (iii) and (iv) for each object set in the plurality of object sets;

(vi) determining whether a value for an objective function has improved relative to a value for the objective function before step (v); and repeating steps (i), (ii), (iii), and (iv) for a different subcombination of object groups in the plurality of object groups when the objective function has improved; and terminating the optimizing step (E), when the objective function has not improved.

54. The method of claim 45, the method further comprising outputting the plurality of object groups to a user interface device, a computer readable storage medium, a memory, or a local or remote computer system; or displaying the plurality of object groups.

55. The method of claim 1, the method further comprising:

(E) performing the method of:

(i) adding a target object group to the plurality of object groups for a target object in the plurality of objects sets that is marked untreated, wherein the target object is added to the target object group and marked treated; and (ii) repeating steps (B) and (C) for the target object group; and (F) repeating step (E) until no object that is marked untreated remains in any object set in the plurality of object sets.

* * * * *